US007919125B2

(12) United States Patent
Tripp et al.

(10) Patent No.: US 7,919,125 B2
(45) Date of Patent: *Apr. 5, 2011

(54) MODULATION OF INFLAMMATION BY HOPS FRACTIONS AND DERIVATIVES

(75) Inventors: Matthew L. Tripp, Gig Harbor, WA (US); John G. Babish, Brooktondale, NY (US); Jeffrey S. Bland, Fox Island, WA (US); Gary K. Darland, Port Orchard, WA (US); Robert Lerman, Gig Harbor, WA (US); Daniel O. Lukaczer, Gig Harbor, WA (US); DeAnn J. Liska, Tacoma, WA (US); Terrence M. Howell, Jamaica Plain, MA (US)

(73) Assignee: Metaproteomics, LLC, San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/755,533

(22) Filed: Apr. 7, 2010

(65) Prior Publication Data
US 2011/0021638 A1 Jan. 27, 2011

Related U.S. Application Data

(60) Continuation of application No. 11/344,559, filed on Jan. 30, 2006, now Pat. No. 7,722,903, which is a division of application No. 10/464,834, filed on Jun. 18, 2003, which is a continuation-in-part of application No. 10/400,293, filed on Mar. 26, 2003, now abandoned, and a continuation-in-part of application No. 10/401,283, filed on Mar. 26, 2003, now abandoned, said application No. 10/464,834 is a continuation-in-part of application No. 09/885,721, filed on Jun. 20, 2001, now Pat. No. 7,205,151.

(60) Provisional application No. 60/450,237, filed on Feb. 25, 2003, provisional application No. 60/420,383, filed on Oct. 21, 2002.

(51) Int. Cl.
*A01N 65/00* (2009.01)
(52) U.S. Cl. ........................................ 424/725
(58) Field of Classification Search .................. None
See application file for complete search history.

(56) References Cited

U.S. PATENT DOCUMENTS

| 3,451,821 A | 6/1969 | Todd et al. |
| 3,552,975 A | 1/1971 | Worden et al. |
| 3,720,517 A | 3/1973 | Bavisotto et al. |
| 3,932,603 A | 1/1976 | Haas |
| 3,933,919 A | 1/1976 | Wilkinson |
| 3,965,188 A | 6/1976 | Westermann et al. |
| 4,123,561 A | 10/1978 | Grant |
| 4,133,903 A | 1/1979 | Thiele et al. |
| 4,148,873 A | 4/1979 | Owades |
| 4,154,865 A | 5/1979 | Grant |
| 4,170,638 A | 10/1979 | Owades |
| 4,389,421 A * | 6/1983 | Palamand |
| 4,401,684 A | 8/1983 | Versluys |
| 4,473,551 A | 9/1984 | Schinitsky |
| 4,554,170 A | 11/1985 | Panzer et al. |
| 4,644,084 A | 2/1987 | Cowles et al. |
| 4,692,280 A | 9/1987 | Spinelli |
| 4,758,445 A * | 7/1988 | Klusters |
| 4,767,640 A | 8/1988 | Goldstein et al. |
| 4,857,554 A | 8/1989 | Kallimanis |
| 5,006,337 A | 4/1991 | Motitschke et al. |
| 5,013,571 A | 5/1991 | Hay |
| 5,041,300 A | 8/1991 | Todd, Jr. et al. |
| 5,073,396 A | 12/1991 | Todd, Jr. |
| 5,082,975 A | 1/1992 | Todd, Jr. et al. |
| 5,155,276 A | 10/1992 | Paul |
| 5,166,449 A | 11/1992 | Todd, Jr. et al. |
| 5,264,236 A | 11/1993 | Ogasahara et al. |
| 5,286,506 A | 2/1994 | Millis et al. |
| 5,296,637 A | 3/1994 | Ting et al. |
| 5,370,863 A * | 12/1994 | Barney et al. |
| 5,387,425 A | 2/1995 | Hsu et al. |
| 5,604,263 A | 2/1997 | Tobe et al. |
| 5,641,517 A | 6/1997 | Eskeland et al. |
| 5,827,895 A | 10/1998 | Nutter et al. |
| 5,866,162 A * | 2/1999 | Grattan |
| 5,919,813 A * | 7/1999 | De Juan |
| 5,968,539 A | 10/1999 | Beerse et al. |
| 6,020,019 A | 2/2000 | Ting et al. |
| 6,129,907 A | 10/2000 | Sreenivasan et al. |
| 6,200,594 B1 | 3/2001 | Ernest et al. |

(Continued)

FOREIGN PATENT DOCUMENTS

CN        1203268        12/1998

(Continued)

OTHER PUBLICATIONS

Abel-salam et al., Pharmacological Research, England 47(4), pp. 311-340 (Apr. 2003).
Albal, MV., et al., "Clinical evaluation of berberine in mycotic infections." Indian J. Ophthalmol 34:91-2 (1986).
Anto, et al., "Anti-inflammatory Activity of Natural and Synthetic Curcuminoids", Pharmacy and Pharmacology Communications, 4(2), pp. 103-106 (1998).
Baldermann et al., J. Chromatography A 1192(1):191-3 (May 23, 2008) (Epub Apr. 8, 2008); abstract only (1 page).
Bermejo, et al. Rev. Esp. Enferm. Dig. 95(9): 621-624 and 625-628 (2003).

(Continued)

*Primary Examiner* — Michael V Meller
(74) *Attorney, Agent, or Firm* — McDermott Will & Emery, LLP

(57) ABSTRACT

A natural formulation of compounds that would to modulate inflammation is disclosed. The formulation would also inhibit expression of COX-2, inhibit synthesis of prostaglandin selectively in target cells, and inhibit inflammatory response selectively in target cells. The compositions containing at least one fraction isolated or derived from hops.

4 Claims, 5 Drawing Sheets

U.S. PATENT DOCUMENTS

| | | | |
|---|---|---|---|
| 6,210,701 B1* | 4/2001 | Darland et al. |
| 6,224,871 B1* | 5/2001 | Hastings et al. |
| 6,264,995 B1* | 7/2001 | Newmark et al. |
| 6,291,483 B1* | 9/2001 | Upadhyay et al. |
| 6,383,527 B1 | 5/2002 | Artman et al. |
| 6,391,346 B1 | 5/2002 | Newmark et al. |
| 6,440,465 B1 | 8/2002 | Meisner |
| 6,447,762 B1 | 9/2002 | Galcerá |
| 6,482,456 B1* | 11/2002 | Yokoo et al. |
| 6,492,429 B1* | 12/2002 | Graus et al. |
| 6,583,322 B1 | 6/2003 | Shalai et al. |
| 6,689,388 B2* | 2/2004 | Kuhrts |
| 6,790,459 B1* | 9/2004 | Cheng et al. |
| 6,801,860 B1 | 10/2004 | Dessen et al. |
| 7,144,590 B2* | 12/2006 | Khurts |
| 7,195,785 B2* | 3/2007 | Babish et al. |
| 7,205,151 B2* | 4/2007 | Babish et al. |
| 7,270,835 B2* | 9/2007 | Tripp et al. |
| 7,279,185 B2* | 10/2007 | Babish et al. |
| 7,332,185 B2* | 2/2008 | Babish et al. |
| 7,431,948 B2* | 10/2008 | Tripp et al. |
| 2002/0028852 A1* | 3/2002 | Ghai et al. |
| 2002/0076452 A1 | 6/2002 | Babish et al. |
| 2002/0077299 A1 | 6/2002 | Babish et al. |
| 2002/0086062 A1 | 7/2002 | Kuhrts |
| 2002/0086070 A1 | 7/2002 | Kuhrts |
| 2002/0156087 A1* | 10/2002 | Nuss et al. |
| 2003/0003212 A1* | 1/2003 | Chien et al. |
| 2003/0008021 A1* | 1/2003 | Babish et al. |
| 2003/0035851 A1* | 2/2003 | Chen |
| 2003/0077313 A1 | 4/2003 | Schwartz et al. |
| 2003/0096027 A1 | 5/2003 | Babish et al. |
| 2003/0113393 A1 | 6/2003 | Babish et al. |
| 2003/0133958 A1 | 7/2003 | Kuno et al. |
| 2003/0180402 A1* | 9/2003 | Jia et al. |
| 2003/0228369 A1* | 12/2003 | Kuhrts |
| 2004/0072900 A1 | 4/2004 | Artman et al. |
| 2004/0086580 A1 | 5/2004 | Tripp et al. |
| 2004/0115290 A1* | 6/2004 | Tripp et al. |
| 2004/0137096 A1 | 7/2004 | Kuhrts |
| 2004/0151792 A1* | 8/2004 | Tripp et al. |
| 2004/0219240 A1 | 11/2004 | Babish et al. |
| 2005/0042317 A1* | 2/2005 | Babish et al. |
| 2005/0129791 A1* | 6/2005 | Babish et al. |
| 2005/0191375 A1* | 9/2005 | Babish et al. |
| 2005/0192356 A1* | 9/2005 | Babish et al. |
| 2006/0127511 A1* | 6/2006 | Tripp et al. |
| 2006/0127512 A1* | 6/2006 | Tripp et al. |
| 2006/0127513 A1 | 6/2006 | Tripp et al. |
| 2006/0127514 A1 | 6/2006 | Tripp et al. |
| 2006/0127515 A1 | 6/2006 | Tripp et al. |
| 2006/0127516 A1 | 6/2006 | Tripp et al. |
| 2006/0127517 A1 | 6/2006 | Tripp et al. |
| 2006/0193933 A1 | 8/2006 | Tripp et al. |
| 2006/0233902 A1 | 10/2006 | Yajima et al. |
| 2007/0003646 A1 | 1/2007 | Kuhrts |
| 2007/0020352 A1 | 1/2007 | Tripp et al. |
| 2007/0160692 A1 | 7/2007 | Tripp et al. |
| 2007/0166418 A1 | 7/2007 | Tripp et al. |
| 2007/0172532 A1 | 7/2007 | Babish et al. |
| 2007/0184133 A1 | 8/2007 | Tripp et al. |
| 2008/0127720 A1 | 6/2008 | Pauli et al. |
| 2008/0248131 A1 | 10/2008 | Tripp et al. |
| 2009/0118373 A1 | 5/2009 | Tripp et al. |

FOREIGN PATENT DOCUMENTS

| | | | |
|---|---|---|---|
| DE | 1901277 | | 8/1970 |
| DE | 2212148 | * | 9/1972 |
| DE | 3931147 | * | 3/1991 |
| DE | 19841615 | * | 3/2000 |
| EP | 0229022 | | 7/1987 |
| EP | 0606599 A1 | | 7/1994 |
| EP | 0681029 A2 | | 11/1995 |
| EP | 1481671 | | 12/2004 |
| EP | 1543834 | | 6/2005 |
| EP | 1 938 828 | | 7/2008 |
| GB | 2330076 | | 4/1999 |
| JP | 52145509 | | 12/1977 |
| JP | 58009084 | | 2/1983 |
| JP | 59059623 | | 4/1984 |
| JP | 363211219 | * | 9/1988 |
| JP | 04202138 | * | 7/1992 |
| JP | 6312924 | * | 11/1994 |
| JP | 07165583 | | 6/1995 |
| JP | 07194351 | * | 8/1995 |
| JP | 8073369 | * | 3/1996 |
| JP | 08073369 | | 3/1996 |
| JP | 9067245 | * | 3/1997 |
| JP | 09502202 | | 3/1997 |
| JP | 410025247 | * | 1/1998 |
| JP | 10152428 | * | 6/1998 |
| JP | 10179129 | | 7/1998 |
| JP | 11246399 | | 9/1999 |
| JP | 11513037 | | 11/1999 |
| JP | 11335231 | | 12/1999 |
| JP | 2001161338 | | 6/2001 |
| JP | 2002-12550 | | 1/2002 |
| JP | 2002-505296 | | 2/2002 |
| RU | 2045955 | * | 10/1995 |
| SU | 1247011 | * | 7/1986 |
| WO | WO 9507079 | | 3/1995 |
| WO | WO 97/31630 | | 9/1997 |
| WO | WO 9749405 | | 12/1997 |
| WO | WO 99/44623 | | 9/1999 |
| WO | WO99/44623 | * | 9/1999 |
| WO | WO 99/61038 | | 12/1999 |
| WO | WO 00/68356 | * | 11/2000 |
| WO | WO 00/74696 | | 12/2000 |
| WO | WO00/74696 | * | 12/2000 |
| WO | WO 02/02582 | | 1/2002 |
| WO | WO02/02582 | * | 1/2002 |
| WO | WO 02/32234 | | 4/2002 |
| WO | WO 03/000185 | | 1/2003 |
| WO | WO 03/035007 | | 5/2003 |
| WO | WO 03/068205 | | 8/2003 |
| WO | WO 03/075943 | | 9/2003 |
| WO | WO 03/082249 | | 10/2003 |
| WO | WO 2004/037180 | | 5/2004 |
| WO | WO 2004/062611 | | 7/2004 |
| WO | WO 2005/084230 | | 9/2005 |
| WO | WO 2006/053249 | | 5/2006 |
| WO | WO 2006/062681 | | 6/2006 |
| WO | WO 2007/067812 | | 6/2007 |
| ZA | 200000857 | | 8/2001 |

OTHER PUBLICATIONS

Bolick D et al., Endocrinology 144(12), pp. 5227-5231 (Dec. 2003).
Byrne, et al. J. Chem. Soc. (C):2810 (1971).
Carson, J. Am. Chem. Soc. 73:1850-1851 (1951).
Chattopadhyay et al., Current Science, 87(1) (Jul. 10, 2004).
Chen Wei-Jen et al., Journal of Agricultural and Food Chemistry 52(1), pp. 55-64 (Jan. 1, 2004).
Chou, et al. Eur. J. Biochem. 115:207-216 (1981).
Chou, et al., TIPS, pp. 450-454, Nov. 1983.
Cohen, Protein Kinases—the major drug targets of the twenty-first century? Nature Reviews, 1: 309-315 (2002).
De Keukeleire "Fundamentals of Beer and Hop Chemistry" Quimica Nova, 23(1) pp. 108-112 (2000).
EP Search Report for EP App. No. 07809709.4.
European Search Report EP 05 723 839.6.
European Search Report for corresponding EP Application No. 02737562.5 (4 pages).
European Search Report for related European Application No. 02784313.5.
Exercise as Treatment for Arthritis, Rheumatic and Immunologic Diseases, Cleveland Clinic, www.clevelandclinic.org, Mar. 14, 2000.
Extended European Search Report EP 10162893.1.
Extended European Search Report EP 07717798.8.
Extended European Search Report EP 07809708.6.
Foucault et al., J. Chromatography A 808(1-2):3-22 (May 29, 1998); abstract only (3 pages).
Gao et al., J. Food Sci. Nutr. vol. 9, pp. 240-244 (2004).
Gerhauser, Beer Constituents as Potential Cancer Chemopreventive Agents, EP Journal of Cancer 41; 1941-1954: (2005).

Germany, "The Absolutely German Drink," contents of beer, 2004, 5 pages.
Gilani, "Studies on Antihypertensive and Antispasmodic Activities of Methanol Extract of *Acacia nilotica* Pods", Phytotherapy Research 13: 665-669 (1999).
Information on ArthroTrim™ product, downloaded from Internet Aug. 30, 2002.
Information on "Hops and Beer Flavours", IOB Technical Symposium, Apr. 2001, pp. 1-9.
Information on "Zyflamend and Zyflamend PM", downloaded from Internet Aug. 30, 2002.
International Search Report for Corresponding PCT Application No. PCT/US05/41018; 2pp.
International Search Report for PCT /US06/30920, Aug. 3, 2007, 3 pages.
International Search Report for PCT/US06/47196.
Jafri et al., Pakistan Journal of Science, vol. 61, No. 4, pp. 220-222 (Dec. 2009).
Kaltner, Investigation of formation of Hops Aroma and technological Measures for Products of Hops-Aromatic Beers, Technical University of Munich, 7 pp. corresponding to Kaltner, D., Technische Universitat Munchen, (Nov. 30, 2000), pp. 1-193, plus Tabs. AH1-A.
Kanematsu, et al. J Bone Miner Res 12(11):1789-1796 (1997).
Konda, et al., Arthritis & Rheumatism 62(6): 1683-1692, (2010).
Lamy Virginie et al., Apoptosis, an Int'l Journal on Programmed Cell Death,13(10), pp. 1232-1242 (Aug. 25, 2008).
Lamy Virginie et al., Carcinogenesis, 28(7), pp. 1575-1581 (Jul. 2007).
Lerman et al, FASEB Journal, Fed. Of American Soc. For Experimental Biol., vol. 18, No. 4-5 (Jan. 1, 2004).
Mannering et al., Food, Nutrition and Chemical Toxicity X(X), pp. 311-323 (Jan. 1, 1993).
Minich et al., Journal of nutrition and Metabolism, vol. 2010, article ID 467316, pp. 1-11, (2010).
Newark, et al., "Beyond Aspirin", pp. 147-151, Hohm Press (2000).
Office Action issued for U.S. Appl. No. 11/667,614 mailed Apr. 16, 2010.
Office Action issued for U.S. Appl. No. 11/667,615 mailed Mar. 16, 2010.
Office Action issued for U.S. Appl. No. 11/701,583 mailed Feb. 8, 2008.
Office Action issued for U.S. Appl. No. 11/701,583 mailed Jul. 6, 2009.
Office Action issued for U.S. Appl. No. 11/701,583 mailed Nov. 26, 2008.
Office Action issued in U.S. Appl. No. 10/464,834 on Aug. 3, 2010.
Office Action issued in U.S. Appl. No. 10/532,388 on Mar. 26, 2010.
Office Action issued in U.S. Appl. No. 10/590,301 on Aug. 19, 2010.
Office Action issued in U.S. Appl. No. 10/590,424 on Jun. 29, 2010.
Office Action issued in U.S. Appl. No. 10/789,814 on Jun. 11, 2010.
Office Action issued in U.S. Appl. No. 11/344,556 on Sep. 3, 2010.
Office Action issued in U.S. Appl. No. 11/344,556 on Dec. 16, 2009.
Office Action issued in U.S. Appl. No. 11/344,556 on Mar. 27, 2009.
Office Action issued in U.S. Appl. No. 11/344,557 on Mar. 25, 2010.
Office Action issued in U.S. Appl. No. 11/344,557 on Apr. 21, 2008.
Office Action issued in U.S. Appl. No. 11/344,557 on Aug. 28, 2009.
Office Action issued in U.S. Appl. No. 11/344,557 on Jan. 10, 2007.
Office Action issued in U.S. Appl. No. 11/344,557 on Sep. 26, 2007.
Office Action issued in U.S. Appl. No. 11/649,584 on Mar. 3, 2010.
Office Action issued in U.S. Appl. No. 11/344,552 on Sep. 8, 2010.
Office Action issued in U.S. Appl. No. 11/501,393 on Aug. 25, 2010.
Office Action issued in U.S. Appl. No. 12/030,335 on Oct. 21, 2010.
Office Action issued in U.S. Appl. No. 11/636,867 on Aug. 30, 2010.
Office Action issued in U.S. Appl. No. 11/729,696 on Mar. 25, 2010.
Pairet, et al. Inflamm. Res 47(Supp. 2), s93-s101 (1998).
Panglisch, Monafsschrift fuer Brauwissen Schaft, 43(1), 4-16 (1990).
Parts per Milliion, 1 page, 2004.
Pippa, et al. Scand. J. Gastroenterol. Suppl. 167:32-35 (1989).
Poullis ,et al. J. Gastroenterol. Hepatol. 18:756-762 (2003).
Provital Group, Rosemary-eco Botany, 2007, 9 pages.
Q & A, (what does ppm or ppb mean?) 3 pages, 2004.

Rahman, M.M., et al., "Conjugated linoleic acid inhibits osteoclast differentiation of RAW264.7 cells by modulating RANKL signaling" J. Lipid Res., 47(8): 1739-1748, (2006).
Smith, et al., Natural Foam Stabilizing and Bittering Compounds Derived From Hops, Journal of the American Society of Brewing Chemists, vol. 56, No. 2, 1998, pp. 52-57.
Stephan T E et al., Biochemical Pharmacology, 55(4), pp. 505-514, (Feb. 15, 1998).
Stevens, Xanthohumol and related Prenylflavonoids from Hops and Beer: To Your Good Health, Science Direct, 2pp (2004).
Suh, et al. Cancer Res 58:717-723 (1988).
Supplemental European Search Report for EP 07845228.
Supplementary European Search Report from related EP Application No. 05851567, 8PP.
Supplementary Partial European Search Report for related European Patent Application No. 05723895.8, 5 pages (2007).
Tagashira M et al., Bioscience, Biotechnology, and Biochemistry, 59(4), pp. 740-742 (Apr. 1995).
The national. 3 pages (1999).
Turmeric: The Ayurvedic Spice of Life, published at www.bioponic.com/pdfs/TurmericAyurveda.pdf (2003).
US News and world report re Palliative Care, 10 pages (2008).
Van Montfrans et al. Inflammatory Signal Transduction in Crohn's Disease and Novel Therapeutic Approaches. Science Direct, Jun. 2, 2002, 20 pages. Biochemical Pharmacology, vol. 64, issues 5-6.
Vanhoenacker, et al., Journal of Chromatography, vol. 1035, No. 1, (Apr. 30, 2004), pp. 53-61.
Verzele, et al. Chemistry and analysis of hop and beer bitter acids, Developments in food science, 27, pp. 44-51, 88-139 (1991).
Verzele and De Keukeleire (eds.) Chemistry and Analysis of Hop and Beer Bitter Acids; Elsevier, Chapters 5, 20 pages (1991).
Verzele and De Keukeleire (eds.) Chemistry and Analysis of Hop and Beer Bitter Acids; Elsevier, Chapters 6, 8 pages (1991).
Wang, et al. Free Radical Biology & Medicine 27:612-616 (1999).
Ward, et al., Therapeutic Potential of Phosphoinositide 3-Kinase Inhibitors, Chemistry & Biology, vol. 10, 207-210, Mar. 2003.
Written Opinion for corresponding PCT Application No. PCT/US05/41018; 3 pp.
Zhao Feng et al., Biological and Pharmaceutical Bulletin, 26(1), pp. 61-65 (Jan. 2003).
"Information on ArthroTrim™ product", downloaded from Internet Aug. 30, 2002.
"Information on Zyflamend and Zyflamend PM", downloaded from Internet Aug. 30, 2002.
"Information on Hops and Beer Flavours", downloaded from internet Feb. 15, 2005.
Anto, et al. Pharm. Pharmacol. Comm. 4:103-106 (1998).
Bermejo, et al. Rev. Esp. Enferm. Dig. 95(9): 625-628 (2003).
Brown, et al. J. Chem. Soc. 545 (1959).
Byrne, et al. J. Chem. Soc. (c):2810-2813 (1971).
Carroccio, et al. Clin. Chem. 49(6):861-867 (2003).
Carson, J., Am. Chem. Soc. 73:1850-1851 (1951).
Chandra, et al. Indian J. Medical Research 60(1):138-142 (1972).
Charlier, et al. Eur. J. Med. Chem. 38:645-659 (2003).
Chou et al. Eur. J. Biochem. 115:207-216 (1981).
Chou, et al. Adv enzyme regul 22:27-55 (1983).
Chou, et al. J. Biol. Chem. 252(18):6438-6442 (1977).
Chou, et al. J. Theor. Biol. 35:285-297 (1972).
Chou, et al. Trends Pharm. Sci. 4:450-454 (1983).
Chou, J. Theor. Biol. 59:253-276 (1976).
Costa, et al. Digest. Liver Dis. 35:642-647 (2003).
Davies, WL. Abstract—Fertiliser, Feeding Stuffs and Farm Supplies J. 11:694 (1926).
Ding, et al. Biochem. Biophy. Res. Comm. 261:218-223 (1999).
Friedman, et al. J Cutan Med. Surg. 6(5):449-159 (2002).
Germany, "The Absolutely German Drink," contents of beer, 2004, 5 pages.
Goldstein, et al. Am. J. Gastroenterol. 96(4):1019-1027 (2001).
Halter, et al. Gut 49:443-453 (2001).
Hamberg, et al. J. Bio. Chem. 246(22):6713-6721 (1971).
Huang, et al. Cancer Res. 51:813-819 (1991).
International Search Report for PCT/US02/19617.
International Search Resort for PCT/US04/16043.

Jach, Przegl Dermatol. 65(4):379-381 (1978).
Kanematsu, et al. J Bone Miner Res 12:1789-1796 (1997).
Lopes, Curr. Med Res Opin. 8(3):145-149 (1982).
Meling, et al. Scand. J. Gastroenterol. 31:339-344 (1996).
Noreen, et al. J. Nat. Prod 61:2-7 (1998).
Pairet, et al. Inflamm. Res 47(2), s93-s101 (1998).
Panglisch. monafsschrift fuer brauwissen schaft, 1990, 43(1), 4-16.
Pippa, et al. Scand. J. Gastroenterol. 32-35 (1989).
Plewig, et al. J Invest. Dermatol. 65(6):532-536 (1975).
Poullis, et al. J. Gastroenterol. Hepatol. 18:756-762 (2003).
Ringbom, et al. J. Nat Prod 61:1212-1215 (1998).
Røseth, Digest. Liver Dis. 35:607-609 (2003).
Schjerven, et al. Br. J. Dermatol. 149:484-491 (2003).
Shah. et al. Gut 48:339-346 (2001).
Shimamura, et al. Biochem. Biophys. Res. Comm 289:220-224 (2001).
Shureiqi, et al. Cancer Res 61:6307-6312 (2001).
Sivri, Fundam. Clinic. Pharmacol. 18:23-31 (2004).
Subbaramaiah, et al. Cancer Res. 60:2399-2404 (2000).
Suh, et al. Cancer Res. 58:717-723 (1988).
Tagashira, et al., Biosci. Biotech. Biochem. 59(4):740-742 (1996).
Thomas m. Newmark and paul schulick, Beyond Aspirin nature's answer to arthritis, cancer & alzheimer's disease, hohm press (2000) release 7; pp. 147-151.
Tibble, et al. Drugs Today 37(2):85-96 (2001).
Tibble, et al. Gut 45:362-366 (1999).
Tobe, et al. Biosci. Biotech. Biochem 61(1):158-159 (1997).
Wang, et al. Free Radical Biology & Medicine 27(5/6):612-616 (1999).
Warner, et al. Proc Natl Acad Sci USA 96:7563-7568 (1999).
Yamamoto, et al. Abstract—Prostaglandins & Other Lipid Mediators 59:1-234 (1999).
Yamamoto, FEBS Letters 465:103-106 (2000).
Yui, et al. Biol. Pharm. Bull. 26(6):753-760 (2003).

* cited by examiner

[A]

[B]

[C]

[D]

[E]

MODULATION OF INFLAMMATION BY HOPS FRACTIONS AND DERIVATIVES

CROSS-REFERENCE TO RELATED APPLICATIONS

This patent application is a continuation of U.S. application Ser. No. 11/344,559, filed Jan. 30, 7006, now U.S. Pat. No. 7,722,903 which is a divisional of and claims the priority of U.S. application Ser. No. 10/464,834, filed on Jun. 18, 2003, which is a continuation-in-part of U.S. application Ser. No. 10/400,293. filed Mar. 26, 2003, now abandoned, and a continuation-in-part of U.S. application Ser. No. 10/401.283, filed Mar. 26, 2003, now abandoned, both of which claim the benefit under 35 U.S.C. §119(e) to provisional application No. 60/450,237, filed on Feb. 25, 2003, and provisional application No. 60/420,383, filed on Oct. 21, 2002. U.S. application Ser. No. 10/464,834, filed on Jun. 18, 2003, is also a continuation-in-part of U.S. application Ser. No. 09/885,721, filed Jun. 20, 2001, now U.S. Pat. No. 7,205,151. The contents of each of these earlier applications are hereby incorporated by reference as if recited herein in their entirety

BACKGROUND OF THE INVENTION

1. Field of the Invention

The present invention relates generally to methods of use of a composition comprising hops extracts or derivatives thereof, wherein the compositions can inhibit expression of cyclooxygenase-2 (COX-2), inhibit synthesis of prostaglandins selectively in target cells, and/or inhibit inflammatory response selectively in target cells.

2. Description of the Related Art

Cyclooxygenase (prostaglandin endoperoxide synthase, EC 1.14.991, COX) catalyzes the rate-limiting step in the metabolism of arachidonic acid to prostaglandin $H_2$ ($PGH_2$), which is further metabolized to various prostaglandins, prostacyclin and thromboxane A2 (c.f. FIG. 1). In the early 1990s, it was established that COX exists in two isoforms, commonly referred to as COX-1 and COX-2. It was subsequently determined that the COX-1 and COX-2 proteins are derived from distinct genes that diverged well before birds and mammals. Prostaglandins (PGs) generated via the COX-1 and COX-2 pathways are identical molecules and therefore have identical biological effects. COX-1 and COX-2, however, may generate a unique pattern and variable amounts of eicosanoids; therefore, relative differences in the activation of these isozymes may result in quite dissimilar biological responses. Differences in the tissue distribution and regulation of COX-1 and COX-2 are now considered crucial for the beneficial as well as adverse effects of COX inhibitors.

The generally held concept (COX dogma) is that COX-1 is expressed constitutively in most tissues whereas COX-2 is the inducible enzyme triggered by pro-inflammatory stimuli including mitogens, cytokines and bacterial lipopolysaccharide (LPS) in cells in vitro and in inflamed sites in vivo. Based primarily on such differences in expression, COX-1 has been characterized as a housekeeping enzyme and is thought to be involved in maintaining physiological functions such as cytoprotection of the gastric mucosa, regulation of renal blood flow, and control of platelet aggregation. COX-2 is considered to mainly mediate inflammation, although constitutive expression is found in brain, kidney and the gastrointestinal tract. Therefore, it would be desirable to down-regulate tissue-specific or cell-specific expression of COX-2.

Arachidonic acid serves as the primary substrate for the biosynthesis of all PGs. PGs are ubiquitous hormones that function as both paracrine and autocrine mediators to affect a myriad of physiological changes in the immediate cellular environment. The varied physiological effects of PGs include inflammatory reactions such as rheumatoid arthritis and osteoarthritis, blood pressure control, platelet aggregation, induction of labor and aggravation of pain and fever. The discovery 30 years ago that aspirin and other non-steroidal analgesics inhibited PG production identified PG synthesis as a target for drug development. There are at least 16 different PGs in nine different chemical classes, designated PGA to PG1. PGs are part of a larger family of 20-carbon-containing compounds called eicosanoids; they include prostacyclins, thromboxanes, and leukotrienes. The array of PGs produced varies depending on the downstream enzymatic machinery present in a particular cell type. For example, endothelial cells produce primarily $PGI_2$, whereas platelets mainly produce $TXA_2$.

Prostaglandins (PG) are believed to play an important role in maintenance of human gastric mucosal homeostasis. Current dogma is that COX-1 is responsible for PG synthesis in normal gastric mucosa in order to maintain mucosal homeostasis and that COX-2 is expressed by normal gastric mucosa at low levels, with induction of expression during ulcer healing, following endotoxin exposure or cytokine stimulation. It now appears that both COX-1 and COX-2 have important physiological roles in the normal gastric mucosa.

Compounds that inhibit the production of PGs by COX have become important drugs in the control of pain and inflammation. Collectively these agents are known as non-steroidal anti-inflammatory drugs (NSAIDs) with their main indications being osteoarthritis and rheumatoid arthritis. However, the use of NSAIDs, and in particular aspirin, has been extended to prophylaxis of cardiovascular disease. Over the last decade, considerable effort has been devoted to developing new molecules that are direct inhibitors of the enzymatic activity of COX-2, with the inference that these compounds would be less irritating to the stomach with chronic use. Therefore, it would be desirable to inhibit inflammation response selectively in target cells.

U.S. patent application 2002/0086070A1 of Kuhns entitled, "ANTI-INFLAMMATORY AND CONNECTIVE TISSUE REPAIR FORMULATIONS" describes a hops component that has an $IC_{50}$-WHMA COX-2/COX-1 ratio ranging from about 0.23 to about 3.33. Example 1 of the application describes a composition containing an extract obtained through supercritical carbon dioxide extraction of whole hops ($CO_2$-extract) comprising 42% humulone.

U.S. Pat. No. 6,391,346 entitled, "ANTI-INFLAMMATORY, SLEEP-PROMOTING HERBAL COMPOSITION AND METHOD OF USE" describes an orally administered composition capable of reducing inflammation in animals, while promoting sleep for such animals. The composition contains hydroalcoholic extract of hops and supercritical carbon dioxide extract of hops which are used to promote sleep.

An ideal formulation for the treatment of inflammation would inhibit the induction and activity of COX-2 without inhibiting the synthesis of $PGE_2$ in gastric mucosal cells. However, conventional non-steroidal anti-inflammatory drugs lack the specificity of inhibiting COX-2 without affecting gastric $PGE_2$ synthesis and are at risk to cause damages on the gastrointestinal system, when used for extended periods. Indeed, even the newly developed, anti-inflammatory drugs such as rofecoxib and celexocib produce untoward gastric toxicity in the form of induced spontaneous bleeding and delay of gastric ulcer healing.

Thus, it would be useful to identify a formulation of compounds that would specifically inhibit or prevent the synthesis of prostaglandins by COX-2 with little or no effect on synthesis of $PGE_2$ in the gastric mucosa. Such a formulation, which would be useful for preserving the health of joint tissues, for treating arthritis or other inflammatory conditions, has not previously been discovered. The term "specific or selective COX-2 inhibitor" was coined to embrace compounds or mixtures of compounds that selectively inhibit COX-2 over COX-1. However, while the implication is that such a calculated selectivity will result in lower gastric irritancy, unless the test materials are evaluated in gastric cells, the term "selective COX-2 inhibitor" does not carry assurance of safety to gastrointestinal cells. Only testing of compound action in target tissues, inflammatory cells and gastric mucosal cells, will identify those agents with low potential for stomach irritation.

The major problem associated with ascertaining COX-2 selectivity (i.e. low gastric irritancy) is that differences in assay methodology can have profound effects on the results obtained. Depicted in Table 1 are the categories of the numerous in vitro assays that have been developed for testing and comparing the relative inhibitory activities of NSAID acrd natural compounds against COX-1 and COX-2. These test systems can be classified into three groups: (1) systems using animal enzymes, animal cells or cell lines, (2) assays using human cell lines, or human platelets and monocytes, and (3) currently evolving models using human cells that are representative of the target cells for the anti-inflammatory and adverse effects of NSAID and dietary supplements. Generally, models using human cell lines or human platelets and monocytes are the current standard and validated target cell models have not been forthcoming. A human gastric cell line capable of assessing potential for gastric irritancy is a need.

TABLE 1

Classification of test systems for in vitro assays assessing COX-2 selectivity of anti-inflammatory compounds†

TEST SYSTEMS

| ANIMAL | HUMAN | TARGET |
| --- | --- | --- |
| Enzymes | Enzymes | Human Gastric Mucosa Cells |
| Cells | Cells | Human Chondrocytes |
| Cell lines | Cell lines | Human Synoviocytes |

OTHER SYSTEM VARIABLES

| | |
| --- | --- |
| 1. | Source of arachidonic acid-endogenous or exogenous; |
| 2. | Various expression systems for gene replication of COX-1 and COX-2; |
| 3. | The presence or absence of a COX-2 inducing agent; |
| 4. | COX-2 inducing agents are administered at different concentrations and for different periods of time; |
| 5. | Duration of incubation with the drug or with arachidonic acid; |
| 6. | Variation in the protein concentration in the medium. |

†Adapted from Pairet, M. and van Ryn, J. (1998) Experimental models used to investigate the differential inhibition of cyclooxygenase-1 and cyclooxygenase-2 by non-steroidal anti-inflammatory drugs. Inflamm. Res 47, Supplement 2S93-S101 and incorporated herein by reference.

The enzymes used can be of animal or human origin, they can be native or recombinant, and they can be used either as purified enzymes, in microsomal preparations, or in whole-cell assays. Other system variables include the source of arachidonic acid. PG synthesis can be measured from endogenously released arachidonic acid or exogenously added arachidonic acid. In the later case, different concentrations are used in different laboratories.

Second, there are various expression systems for gene replication of recombinant COX-1 and COX-2 enzymes. In addition, the cells transfected with the Cox-1 or Cox-2 gene can be of diverse origins, for instance, insect cell lines or COS cells.

Third, the absence or presence of a COX-2 inducing agent can vary. Cells that are stably transfected with the recombinant enzymes express this enzyme constitutively and no inducing agent is used. This is in fundamental contrast with other cells in which COX-2 has to be induced. Induction of COX-2 is commonly performed using bacterial LPS or various cytokines such as interleukin-1β or tumor necrosis factor. Additionally, these endotoxins and cytokines are administered at various concentrations.

Fourth, the duration of the incubation with the test agent, the COX-2 inducing agent, or with arachidonic acid varies among different laboratories. These differences can influence the quantitative outcome of the study, because the inhibition of COX-2 is time dependent. Finally, the protein concentration of the medium can vary; this is an issue for compounds that can bind avidly to plasma proteins.

An ideal assay for COX-2 selectivity would have the following characteristics: (1) whole cells should be used that contain native human enzymes under normal physiological control regarding expression; (2) the cells should also be target cells for the anti-inflammatory and adverse effects of the compounds; (3) COX-2 should be induced, thereby simulating an inflammatory process, rather than being constitutively expressed; and (4) PG synthesis should be measured from arachidonic acid released from endogenous stores rather than from exogenously added arachidonic acid.

Differences in methodology for can explain a dramatic difference in the results obtained for COX inhibition. For example, when assayed against the purified enzyme, usolic acid exhibited an $IC_{50}$ of 130 µM, far outside of possible physiologically obtainable concentrations [Ringbom, T. et al. (1998) *Ursolic acid from Plantago major, a selective inhibitor of cyclooxygenase-2 catalyzed prostaglandin biosynthesis. J Nat Prod* 61, 1212-1215]. In the RAW 264.7 marine macrophage line, Suh et al. report an $IC_{50}$ for usolic acid of approximately 40 µM [Suh, N., et al. (1998) *Novel triterpenoids suppress inducible nitric oxide synthase (iNOS) and inducible cyclooxygenase (COX-2) in mouse macrophages. Cancer Res* 58, 717-723]; and in phorbol 12-myristate 13-acetate stimulated human mammary cells, the approximate median inhibitory concentration of usolic acid was 3.0 µM [Subbaramaiah, K. et al. (2000) Ursolic acid inhibits cyclooxygenase-2 transcription in human mammary epithelial cells. *Cancer Res* 60, 2399-2404].

No laboratory has, as yet, developed an ideal assay for COX-2 selectivity. The whole cell system most commonly used for Rx and OTC products is the human whole blood assay developed by the William Harvey Institute [Warner, T. D. et al. (1999) *Nonsteroid drug selectivities for gclo-oxygenase-1 rather than cyclo-oxygenase-2 are associated with human gastrointestinal toxicity: a full in vitro analysis. Proc Natl Acad Sci USA* 96, 7563-7568]. To date, this assay format has developed more data supporting clinical relevance than any other. However, new research in the role of constitutive expression of COX-2 in normal gastric mucosa necessitates revisiting the relevance of the use of platelets to model COX-1 inhibition in the absence of COX-2. The extrapolation of gastrotoxicity from platelets studies is no longer on a sound molecular basis. The validation of a human gastric mucosal cell line for establishing the potential target tissue toxicity of cyclooxygenase inhibitors represents a critical need for the development of safe and effective anti-inflammatory agents.

Therefore, it would be useful to identify a composition that would specifically inhibit or prevent the expression of COX-2 enzymatic activity in inflammatory cells, while having little or no effect on $PGE_2$ synthesis in gastric mucosal cells so that these formulations could be used with no gastrointestinal upset. Furthermore, such formulations should allow for healing of pre-existing ulcerative conditions in the stomach.

SUMMARY OF THE INVENTION

Thus, it would be useful to identify a formulation of compounds that would to modulate the inflammatory response in cells. Such a formulation has widespread applications.

It would also be useful to identify a formulation of compounds that would inhibit expression of COX-2, inhibit prostaglandin synthesis selectively in target cells, or inhibit inflammation response selectively in target cells. For example, it would also be useful to identify a formulation of compounds that would specifically inhibit or prevent the synthesis of prostaglandins by COX-2 in inflammatory cells with little or no effect on $PGE_2$ synthesis in gastric mucosal cells. Such a formulation, which would be useful for preserving the health of joint tissues for treating arthritis or other inflammatory conditions, has not previously been discovered. Preferably, the formulations have a median effective concentration for COX-2 inhibition in inflammatory cells that is minimally ten times greater than the median effective concentration for the inhibition of $PGE_2$ synthesis in gastric cells. For example, if the median inhibitory concentration for COX-2 of a test formulation was 0.2 µg/mL in the murine macrophage RAW 264.7, the formulation would not be considered to have low potential for gastric irritancy unless the median inhibitory concentration for $PGE_2$ synthesis in gastric cells was equal to or greater than 2 µg/mL.

A preferred embodiment comprises compositions containing at least one fraction isolated or derived from hops (*Humulus lupulus*). Examples of fractions isolated or derived from hops are isoalpha acids, reduced isoalpha acids, tetra-hydroisoalpha acids, hexahydroisoalpha acids, beta acids, and spent hops. Preferred compounds of fractions isolated or derived from hops, include, but are not limited to, cohumulone, adhumulone, isohumulone, isocohumulone, isoadhumulone, dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone. Preferred compounds can also bear substituents, such as halogens, ethers, and esters.

Preferred compositions also inhibit the inducibility or activity of COX-2. Preferred compositions also can inhibit prostaglandin synthesis selectively in target cells. Preferred compositions also can inhibit inflammation response selectively in target cells.

The compositions have widespread applications. Preferred compositions can be useful for treating conditions, such as cancer, autoimmune diseases, inflammatory diseases, neurological diseases. Preferred compositions are also believed to be useful for treating conditions, such as HIV-1 infections, rhinovirus infections, and cardiovascular diseases.

Preferred compositions would be useful for, but not limited to, the treatment of inflammation in a subject, and for treatment of other inflammation-associated disorders, such as an analgesic in the treatment of pain and headaches, or as an antipyretic for the treatment of fever. Preferred compositions would be useful to treat arthritis, including but not limited to rheumatoid arthritis, spondyloathopatlries, gouty arthritis, osteoarthritis, systemic lupus erythematosis, and juvenile arthritis.

Preferred compositions would be useful in the treatment of asthma; bronchitis, menstrual cramps, tendonitis, bursitis, and skin-related conditions such as psoriasis, eczema, burns and dermatitis. Preferred compositions also would be useful to treat gastrointestinal conditions such as inflammatory bowel disease, Crohn's disease, gastritis, irritable bowel syndrome and ulcerative colitis and for the prevention or treatment of cancer such as colorectal cancer.

Further, preferred compositions would be useful in treating inflammation in such diseases as vascular diseases, migraine headaches, periarteritis nodosa, thyroiditis, aplastic anemia, Hodgkin's disease, sclerodma, rheumatic fever, type 1 diabetes, myasthenia gravis, multiple sclerosis, sacoidosis, nephrotic syndrome, Behchet's syndrome, polymyositis, gingivitis, hypersensitivity, swelling occurring after injury, myocardial ischemia and the like.

Additionally, preferred compositions would also be useful in the treatment of ophthalmic diseases, such as retinopathies, conjunctivitis, uveitis, ocular photophobia, and of acute injury to the eye tissue. Preferred compositions would also be useful in the treatment of pulmonary inflation, such as that associated with viral infections and cystic fibrosis.

Preferred compositions would also be useful for the treatment of certain nervous system disorders such as cortical dementias including Alzheimer's disease. As inhibitors of COX-2 mediated biosynthesis of $PGE_2$ in inflammatory cells, these compositions would also be useful in the treatment of allergic rhinitis, respiratory distress syndrome, endotoxin shock syndrome, atherosclerosis, and central nervous system damage resulting from stroke, ischemia and trauma.

Preferred embodiments further provides a composition to increase the rate at which glucose or chondrotin sulfate function to normalize joint movement or reduce the symptoms of osteoarthritis.

Preferred embodiments also provide for methods of identifying compositions that would specifically inhibit or prevent the synthesis of prostaglandin by COX-2 in inflammatory cells with little or no effect on $PGE_2$ synthesis in gastric mucosal cells.

DETAILED DESCRIPTION OF THE PREFERRED EMBODIMENT

Figure 1:
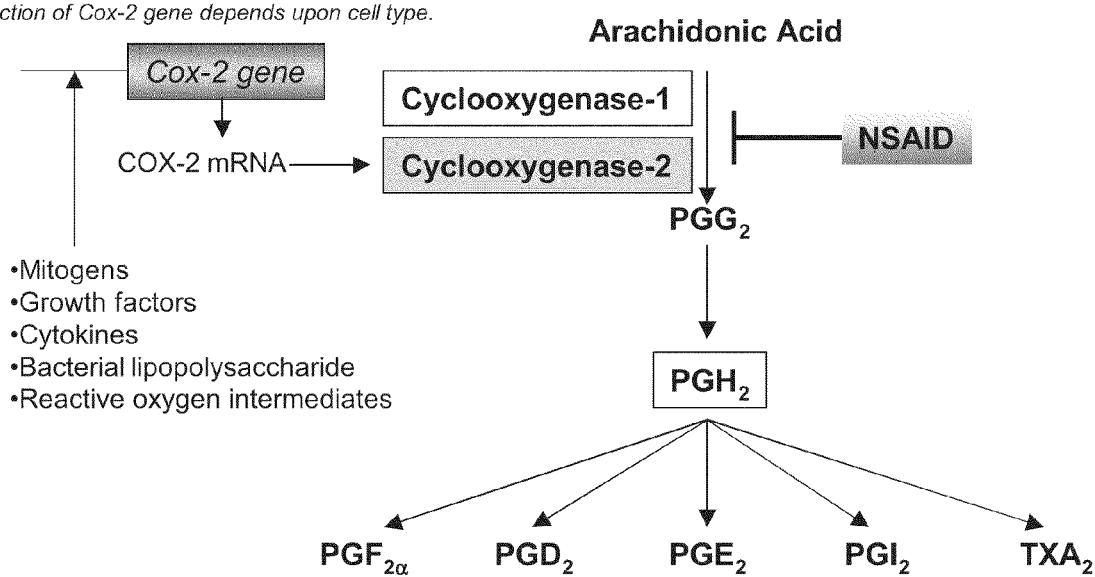
FIG. 1 depicts the induction of cyclooxygenase-2 and the metabolism of arachidonic acid to prostaglandins and other eicosanoids by the cyclooxygenase enzymes. The action of non-steroidal anti-inflammatory agents is through direct inhibition of the cyclooxygenase enzymes.

The present invention relates to the discovery that that a supragenus of components isolated or derived from hops and other compounds result in tissue-specific or cell-specific inhibition of COX-2 expression. Importantly, these compounds are not believed to directly inhibit COX-2 or other enzymes with the prostaglandin synthesis pathway. Preferred embodiments provide compositions and methods for inhibiting COX-2 expression, inhibiting prostanglandin synthesis selectively in target tissues or cells, or inhibiting inflammation response selectively in target tissues or cells.

A preferred embodiment comprises compositions containing fractions or compounds isolated or derived from hops. Examples of fractions isolated or derived from hops are alpha acids, isoalpha acids, reduced isoalpha acids, tetra-hydroisoalpha acids, hexahydroisoalpha acids, beta acids, and spent hops. Preferred compounds of the fractions isolated or derived from hops can be represented by a supragenus below:

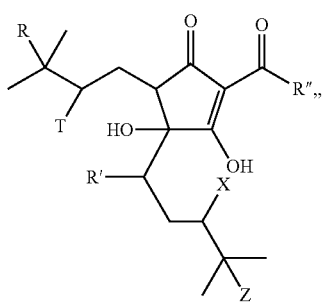

(Supragenus)

wherein R' is selected from the group consisting of carbonyl, hydroxyl, OR, and OCOR, wherein R is alkyl; wherein R" is selected from the group consisting of $CH(CH_3)_2$, $CH_2CH(CH_3)_2$, and $CH(CH_3)CH_2CH_3$; and wherein R, T, X, and Z are independently selected from the group consisting of H, F, Cl, Br, I, and π orbital, with the proviso that if one of R, T, X, or Z is π orbital, then the adjacent R, T, X, or Z is also a π orbital, thereby forming a double bond.

Other preferred compounds of the fractions isolated or derived from hops can be represented by a genus below:

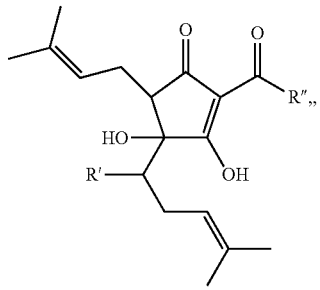

(Genus A)

wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$.

Other preferred compounds of the Fractions isolated or derived from hops can be represented by a genus below:

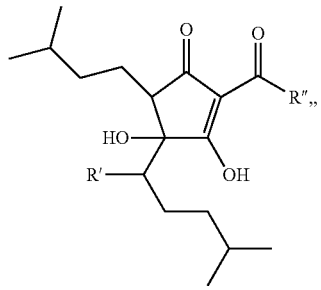

(Genus B)

wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$.

Examples of preferred compounds of an ingredient isolated or derived from hops, include, but are not limited to, humulone, cohumulone, adhumulone, isohumulone, isocohumulone, isoadhumulone, dihydro-isohumulone, dihydro-isocohuxnulone, dihydro-isoadhumulone, tetrahydro-isohumulone, tetrahydro-isocohurulone, tetrahydro-isoadhumulone, hexahydro-isohumulone; hexahydro-isocohumulone, and hexahydro-isoadhumulone. The preferred compounds can bear substituents, as shown in the formula above.

As used herein, the term "dietary supplement" refers to compositions consumed to affect structural or functional changes in physiology. The term "therapeutic composition" refers to any compounds administered to treat or prevent a disease.

As used herein, the term "effective amount" means an amount necessary to achieve a selected result. Such an amount can be readily determined without undue experimentation by a person of ordinary skill in the an.

As used herein, the term "substantial" means being largely but not wholly that which is specified.

As used herein, the term "COX inhibitor" refers to a composition of compounds that is capable of inhibiting the activity or expression of COX-2 enzymes or is capable of inhibiting or reducing the severity, including pain and swelling, of a severe inflammatory response.

As used herein, the terms "derivatives" or a matter "derived" refer to a chemical substance related structurally to another substance and theoretically obtainable from it, i.e. a substance that can be made from another substance. Derivatives can include compounds obtained via a chemical reaction.

As used herein, the term "inflammatory cell" refers to those cellular members of the immune system, for example B and T lymphocytes, neutrophils or macrophages involved in synthesis of prostaglandins in response to inflammatory signals such as interleukins, tumor necrosis factor, bradykinin, histamine or bacterial-derived components.

As used herein, the term "target cells" refers to that cell population in which the inhibition of $PGE_2$ or other prostaglandin synthesis is desired, such as inflammatory cells, tumor cells, or pulmonary cells. Alternatively, "non-target cells" refers to that cell population in which the inhibition of $PGE_2$ or other prostaglandin synthesis is not desired, such as the gastric mucosal, neural or renal cells.

As used herein, the term "hop extract" refers to the solid material resulting from (1) exposing a hops plant product to a solvent, (2) separating the solvent from the hops plant products, and (3) eliminating the solvent.

As used herein, the term "solvent" refers to a liquid of aqueous or organic nature possessing the necessary characteristics to extract solid material from the hop plant product. Examples of solvents would include, but not limited to, water, steam, superheated water, methanol, ethanol, hexane, chloroform, liquid $CO_2$, liquid $N_2$ or any combinations of such materials.

As used herein, the term "$CO_2$ extract" refers to the solid material resulting from exposing a hops plant product to a liquid or supercritical $CO_2$ preparation followed by the removing the $CO_2$.

As used herein, the term "spent hops" refers to the solid and hydrophilic residue from extract of hops.

As used herein, the term "alpha acid" refers to compounds refers to compounds collectively known as humulones and can be isolated from hops plant products including, among others, humulone, cohumulone, adhumulone, hulupone, and isoprehumulone.

As used herein, the term "isoalpha acid" refers to compounds isolated from hops plant products and subsequently have been isomerized. The isomerization of alpha acids can occur thermally, such as boiling. Examples of isoalpha acids include, but are not limited to, isohumulone, isocohumulone, and isoadhumulone.

As used herein, the term "reduced isoalpha acid" refers to alpha acids isolated from hops plant product and subsequently have been isomerized and reduced, including cis and trans forms. Examples of reduced isoalpha acids (RIAA) include, but are not limited to, dihydro-isohumulone, dihydro-isocohumulone, and dihydro-isoadhumulone.

As used herein, the term "tetra-hydroisoalpha acid" refers to a certain class of reduced isoalpha acid. Examples of tetrahydroisoalpha acid (THIAA) include, but are not limited to, tetra-hydro-isohumulone, tetra-hydro-isocohumulone and tetra-hydro-isoadhumulone.

As used herein, the term "hexa-hydroisoalpha acid" refers to a certain class of reduced isoalpha acid. Examples of hexahydroisoalpha acids (HHIAA) include, but are not limited to, hexa-hydro-isohumulone, hexa-hydro-isocohumulone and hexa-hydro-isoadhumulone.

As used herein, the term "beta-acid fraction" refers to compounds collectively known as lupulones including, among others, lupulone, colupulone, adlupulone, tetrahydroisohumulone, and hexahydrocolupulone.

As used herein, the term "essential oil fraction" refers to a complex mixture of components including, among others, myrcene, humulone, beta-caryophyleen, undecane-2-on, and 2-methyl-but-3-en-ol.

As used herein, "conjugates" of compounds means compounds covalently bound or conjugated to a member selected from the group consisting of mono- or disaccharides, amino acids, sulfates, succinate, acetate, and glutathione. Preferably, the mono- or di-saccharide is a member selected from the group consisting of glucose, mannose, ribose, galactose, rhamnose, arabinose, maltose, and fructose.

Hops

Hop extraction in one form or another goes back over 150 years to the early nineteenth century when extraction in water and ethanol was first attempted. Even today an ethanol extract is available in Europe, but by far the predominant extracts are organic solvent extracts (hexane) and $CO_2$ extracts (supercritical and liquid). $CO_2$ (typically at 60 bars pressure and 50 to 10° C.) is in a liquid state and is a relatively mild, non-polar solvent highly specific for hop soft resins and oils. Beyond the critical point, typically at 300 bars pressure and 60° C., $CO_2$ has the properties of both a gas and a liquid and is a much stronger solvent. The composition of the various extracts is compared in Table 2.

TABLE 2

Hop Extracts (Percent W/W)

| Component | Hops | Organic Solvent | Super-Critical $CO_2$ | Liquid $CO_2$ |
|---|---|---|---|---|
| Total resins | 12-20 | 15-60 | 75-90 | 70-95 |
| Alpha-acids | 2-12 | 8-45 | 27-55 | 30-60 |
| Beta-acids | 2-10 | 8-20 | 23-33 | 15-45 |
| Essential oils | 0.5-1.5 | 0-5 | 1-5 | 2-10 |
| Hard resins | 2-4 | 2-10 | 5-11 | None |
| Tannins | 4-10 | 0.5-5 | 0.1-5 | None |
| Waxes | 1-5 | 1-20 | 4-13 | 0-10 |
| Water | 8-12 | 1-15 | 1-7 | 1-5 |

At its simplest, hop extraction involves milling, pelleting and re-milling the hops to spread the lupulin, passing a solvent through a packed column to collect the resin components and finally, removal of the solvent to yield a whole or "pure" resin extract.

The main organic extractants are strong solvents and in addition to virtually all the lupulin components, they extract plant pigments, cuticular waxes, water and water-soluble materials.

Supercritical $CO_2$ is more selective than the organic solvents and extracts less of the tannins and waxes and less water and hence water-soluble components. It does extract some of the plant pigments like chlorophyll but rather less than the organic solvents do. Liquid $CO_2$ is the most selective solvent used commercially for hops and hence produces the most pure whole resin and oil extract. It extracts hardly the hard resins or tannins, much lower levels of plant waxes, no plant pigments and less water and water-soluble materials.

As a consequence of this selectivity and the milder solvent properties, the absolute yield of liquid $CO_2$ extract per unit weight of hops is less than when using the other mentioned solvents. Additionally, the yield of alpha acids with liquid $CO_2$ (89-93%) is lower than that of supercritical $CO_2$ (91-94%) or the organic solvents (93-96%). Following extraction there is the process of solvent removal, which for organic solvents involves heating to cause volatilization. Despite this, trace amounts of solvent do remain in the extract. The removal of $CO_2$, however, simply involves a release of pressure to volatize the $CO_2$.

Figure 2:
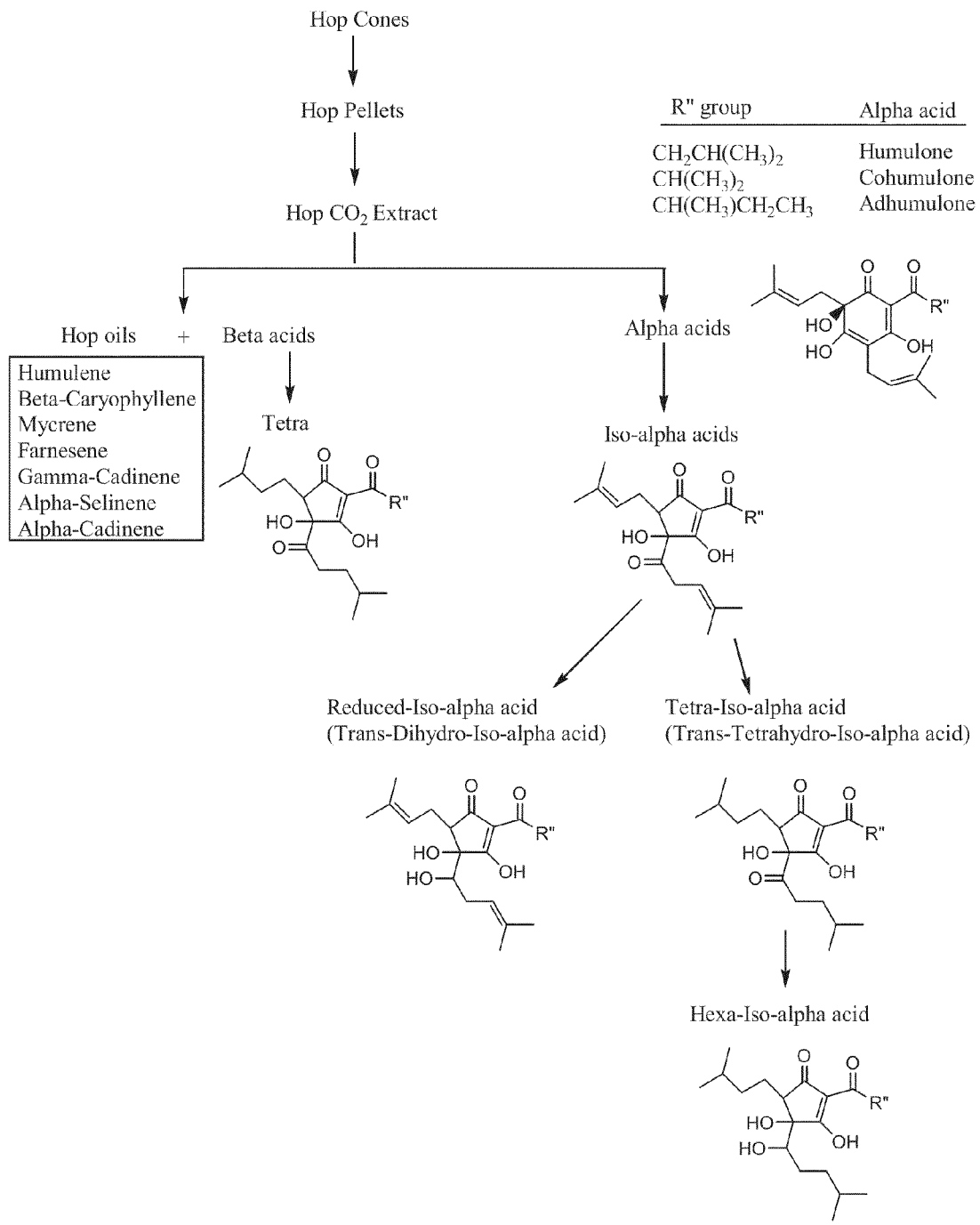
FIG. 2 shows an outline of fractions and compounds that can be obtained from hops.

As shown in FIG. 2, hops $CO_2$ extracts can be fractionated into components, including hops oils, beta acids, and alpha acids. Hops oils include, but not limited to, humulene, beta-caryophyllene, mycrene, farnescene, gamma-cadinene, alphaselinene, and alpha-cadinene. Beta acids include, but are not limited to, lupulone, colupulone, adlupulone, tetrahydroisohumulone, and hexahydrocolupulone, collectively known as lupulones. Beta acids can be isomerized and reduced. Beta acids are reduced to give tetra-beta acids. Alpha acids include, but are not limited to, humulone, cohumulone, adhumulone, hulupone, and isoprehumulone. Alpha acids can be isomerized to give isoalpha acids. Iso-alpha acids can be reduced to give reduced-isoalpha acids, tetra-hydroisoalpha acids, and hexa-hydroisoalpha acids.

A preferred embodiment comprises compositions containing fractions or compounds isolated or derived from hops. Examples of fractions isolated or derived from hops are alpha acids, isoalpha acids, reduced isoalpha acids, tetra-hydroisoalpha acids, hexa-hydroisoalpha acids, beta acids, and spent hops. Preferred compounds of the fractions isolated or derived from hops can be represented by a supragenus below:

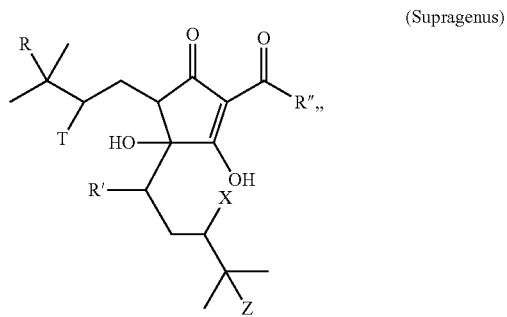

(Supragenus)

wherein R' is selected from the group consisting of carbonyl, hydroxyl, OR, and OCOR, wherein R is alkyl; wherein R" is selected from the group consisting of $CH(CH_3)_2$, $CH_2CH(CH_3)_2$, and $CH(CH_3)CH_2CH_3$; and wherein R, T, X, and Z are independently selected from the group consisting of F, Cl, Br, I, and π orbital, with the proviso that if one of R, T, X, or Z is a π orbital, then the adjacent R, T, X, or Z is also a π orbital, thereby forming a double bond.

Other preferred compounds of the fractions isolated or derived from hops can be represented by a genus below:

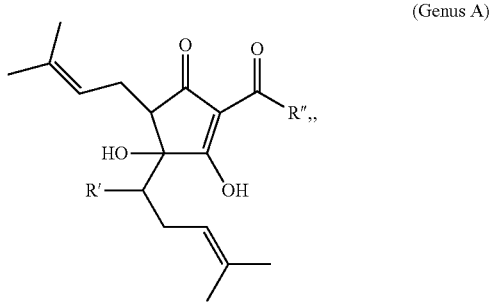

(Genus A)

wherein R' is selected from the group consisting of carbonyl, hydroxyl, OR, and OCOR, wherein R is alkyl; and wherein R." is selected from the group consisting of $CH(CH_3)_2$, $CH_2CH(CH_3)_2$, and $CH(CH_3)CH_2CH_3$.

Other preferred compounds of the fractions isolated or derived from hops can be represented by a genus below:

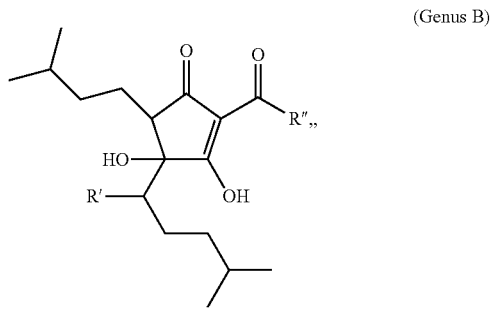

(Genus B)

wherein R' is selected from the group consisting of carbonyl, hydroxyl, OR, and OCOR, wherein R. is alkyl; and wherein R" is selected from the group consisting of $CH(CH_3)_2$, $CH_2CH(CH_3)_2$, and $CH(CH_3)CH_2CH_3$.

Figure 3:
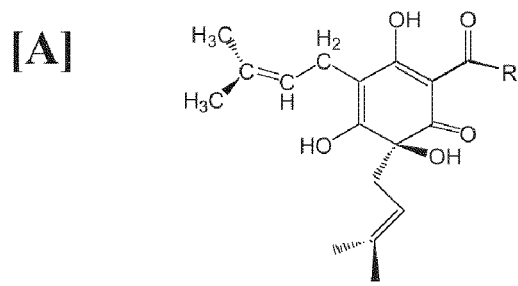
FIG. 3 illustrates [A] the alpha-acid genus (AA) and representative species humulone (R=—$CH_2CH(CH_3)_2$), cohumulone (R=, —$CH(CH_3)_2$), and adhumulone (R=—$CH(CH_3)CH_2CH_3$); [B] the isoalpha acid genus (IAA) and representative species isohumulone (R=—$CH_2(CH_3)_2$), isocohumulone (R=, —$CH(CH_3)_2$), and isoadhumulone (R=—$CH(CH_3)CH_2CH_3$); [C] the reduced isomerized isoalpha acid genus (RIAA) and representative species dihydro-isohumulone (R=—$CH_2CH(CH_3)_2$) dihydro-isocohumulone (R=, —$CH(CH_3)_2$), and dihydro-isoadhumulone (R=—$CH(CH_3)CH_2CH_3$): [D] the tetrahydroisoalpha acid genus (THIAA) and representative species tetra-hydro-isohumulone (R=—$CH_2CH(CH_3)_2$), tetra-hydro-isocohumulone ((R=, —$CH(CH_3)_2$), and tetra-hydro-isoadhumulone (R=—$CH(CH_3)CH_2CH_3$); [E] and the hexa-hydroisoalpha acid (HHIAA) genus with representative species hexa-hydro-isohumulone (R=—$CH_2CH(CH_3)_2$) hexa-hydroisocohumulone (R=, —$CH(CH_3)_2$), and hexa-hydro-isoadhumulone (R=—$CH(CH_3)CH_2CH_3$).
Figure 3:
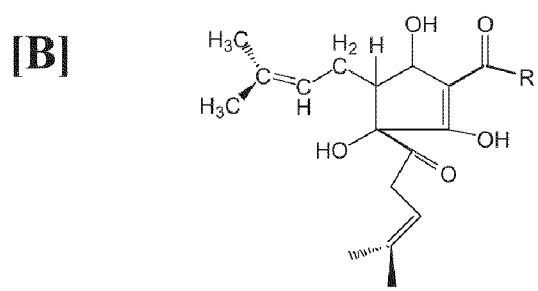
Figure 3:
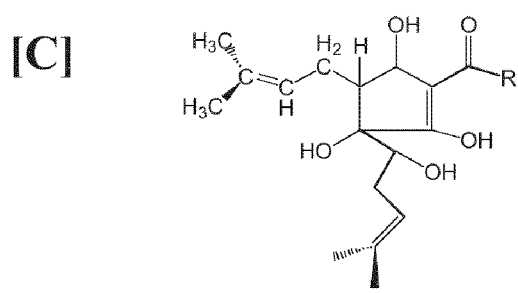
Figure 3:
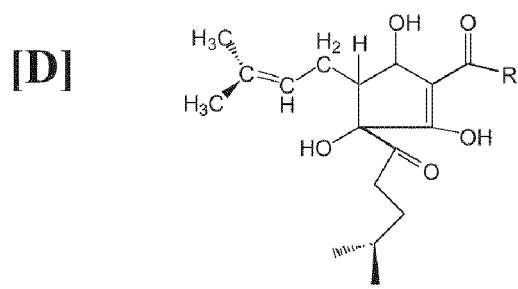
Figure 3:
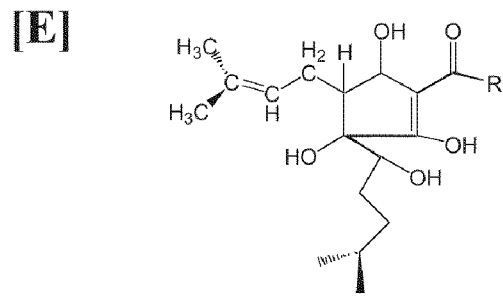

As shown in FIG. 3, examples of preferred compounds of an ingredient isolated or derived from hops, include, but are not limited to, humulone, cohmnulone, adhunulone, isohumulone, isocohumulone, isoadhumulone, dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadlrumulone. The preferred compounds can bear substituents, as shown in the formula above.

The identification of humulone from hops extract as an inhibitor of bone resorption is reported in Tobe, H. et al. 1997. one resorption Inhibitors from hop extract. Biosci, Biotech, Biochem 61(1)158-159.) Later studies by the same group characterized the mechanism of action of humulone as inhibition of COX-2 gene transcription following TNFalpha stimulation of MC3T3, E1 cells [Yamamoto, K. 2000. Suppression of cyclooxygenase-2 gene transcription by humulon of beer hop extract studied with reference to the glucocorticoid receptor. FEBS Letters 465:103-106]. The authors concluded that the action of humulone (also humulon) was similar to that of glucocorticoids, but that humulone did not function through the glucocorticoid receptor. While these results establish that humulone inhibits $PGE_2$ synthesis in MC3T3 cells (osteoblasts) at the gene level, one skilled in the art would not assume that these results would necessarily occur in immune inflammatory cells or other cell lines. Example 5 herein demonstrates the high degree of tissue selectivity of hops compounds and derivatives.

The preferred embodiments also provide compositions and methods for inhibiting expression of COX-2, inhibiting synthesis of prostaglandin selectively in target cells, and inhibiting inflammatory response selectively in target cells. Preferred methods comprise a step of administering to a mammal a composition of the preferred embodiments. Preferred embodiments comprise a fraction isolated or derived from hops. A certain composition comprises alpha acids, isoalpha acids, reduced isoalpha acids, tetrahydroisoalpha acids, hexahydroisoalpha acids, beta acids, or spent hops from hops extract or derivatives thereof. Preferred compounds of the fractions isolated or derived from hops can be represented by a supragenus below:

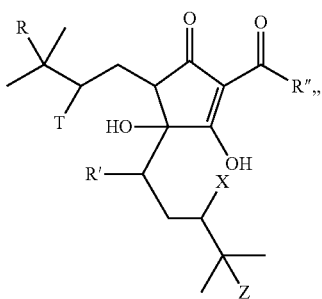

(Supragenus)

wherein R' is selected from the group consisting of carbonyl, hydroxyl, OR, and OCOR, wherein R is alkyl; wherein R" is selected from the group consisting of $CH(CH_3)_2$, $CH_2CH(CH_3)_2$, and $CH(CH_3)CH_2CH_3$; and wherein R, T, X, and Z are independently selected from the group consisting of H, F, Cl, Br, I and π orbital, with the proviso that if one of R, T, X, or Z is a π orbital, then the adjacent R., T, X, or Z is also a π orbital, thereby forming a double bond. Other preferred compounds of the fractions isolated or derived from hops can be represented by a genus below:

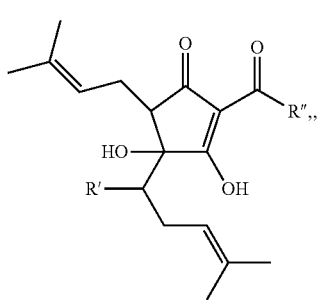

(Genus A)

wherein R' is selected from the group consisting of carbonyl, hydroxyl, OR, and OCOR; wherein R is alkyl; and wherein R" is selected from the group consisting of $CH(CH_3)_2$, $CH_2CH(CH_3)_2$, and $CH(CH_3)CH_2CH_3$. Other preferred compounds of the fractions isolated or derived from hops can be represented by a genus below:

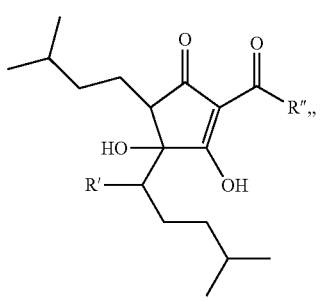

(Genus B)

wherein R' is selected from the group consisting of carbonyl, hydroxyl, OR, and OCOR, wherein R. is alkyl; and wherein R" is selected from the group consisting of $CH(CH_3)_2$, $CH_2CH(CH_3)_2$, and $CH(CH_3)CH_2CH_3$. The preferred embodiments contemplate compositions comprising beta acids or isomerized or reduced beta acids. Preferably, the alpha acid, isoalpha acid, reduced isoalpha acid, tetra-hydroisoalpha acid, hexa-hydroisoalpha acid, beta acid, or spent hops of the preferred embodiments is made from hops extract. More preferably, the alpha acid, isoalpha acid, reduced isoalpha acid, tetra-hydroisoalpha acid, hexa-hydroisoalpha acid, beta acid, or spent hops of the preferred embodiments is made from CO2 extract of hops.

Compositions

The preferred compositions can function to specifically inhibit COX-2 expression, to inhibit prostaglandin synthesis selectively in target cells, or to inhibit inflammation response selectively in target cells. Preferred embodiments include compositions containing fractions or compounds isolated or derived from hops.

A preferred embodiment comprises compositions containing fractions or compounds isolated or derived From hops. Examples of fractions isolated or derived from hops are alpha acids, isoalpha acids, reduced isoalpha acids, tetra-hydroisoalpha acids, hexahydroisoalpha acids, beta acids, and spent hops. Preferred compounds of the fractions isolated or derived from hops can be represented by a supragenus below:

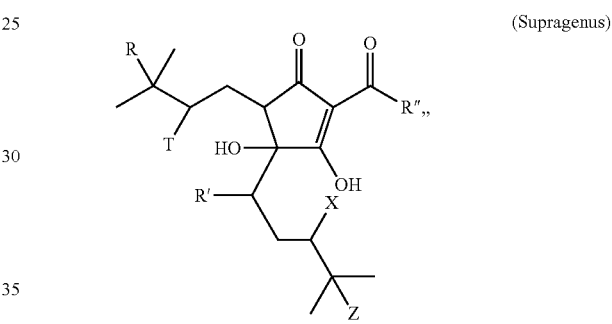

(Supragenus)

wherein R' is selected from the group consisting of carbonyl, hydroxyl, OR, and OCOR, wherein R is alkyl: wherein R" is selected from the group consisting of $CH(CH_3)_2$, $CH_2CH(CH_3)_2$, and $CH(CH_3)CH_2CH_3$; and wherein R, T, X, and Z are independently selected from the group consisting of H, F, Cl, Br, I and π orbital, with the proviso that if one of R, T, X, or Z is a π orbital, then the adjacent R, T, X, or Z is also a π orbital, thereby forming a double bond.

Other preferred compounds of the fractions isolated or derived from hops can be represented by a genus below:

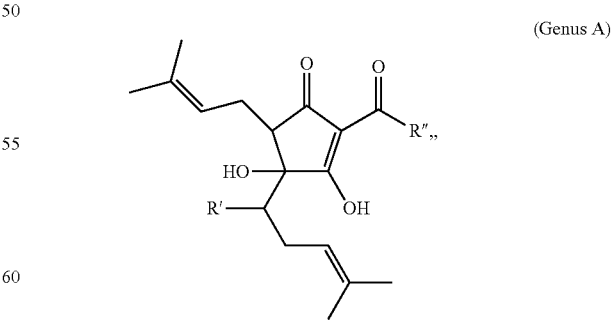

(Genus A)

wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$.

Other preferred compounds of the fractions isolated or derived from hops can be represented by a genus below:

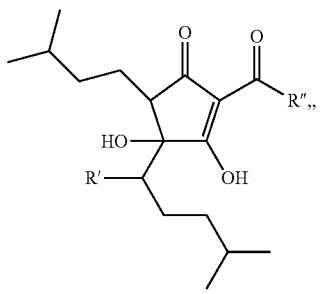

(Genus B)

wherein R' is selected from the group consisting of carbonyl, hydroxyl, OR, and OCOR, wherein R. is alkyl; and wherein R" is selected from the group consisting of CH(CH$_3$)$_2$, CH$_2$CH(CH$_3$)$_2$, and CH(CH$_3$)CH$_2$CH$_3$.

Examples of preferred compounds of an ingredient isolated or derived from hops, include, but are not limited to, humulone, cohumulone, adhumulone, isohumulone, isocohumulone, isoadhumulone, dihydro-isohumulone, dihydroisocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone. The preferred compounds can bear, substituents, as shown in the formula above.

Other embodiments relate to combinations of components. The preferred compositions can also function synergistically to specifically inhibit COX-2 expression, to inhibit prostaglandin synthesis selectively in target cells, or to inhibit inflammation response selectively in target cells.

Dosage

The selected dosage level will depend upon activity of the particular composition, the route of administration, the severity of the condition being treated or prevented, and the condition and prior medical history of the patient being treated. However, it is within the skill of the art to start doses of the composition at levels lower than required to achieve the desired therapeutic effect and to gradually increase the dosage until the desired effect is achieved. If desired, the effective daily dose may be divided into multiple doses for purposes of administration, e.g., two to four separate doses per day. It will be understood, however, that the specific dose level for any particular patient will depend upon a variety of factors including body weight, general health, diet, time and route of administration, combination with other compositions and the severity of the particular condition being treated or prevented.

Preferred embodiments include delivering an effective amount of hops fractions, hops compounds, or hops derivatives alone or with in combination with other active ingredients. Preferably, a daily dose of preferred compositions would be formulated to deliver about 0.5 to 10,000 mg of alpha acid, isoalpha acid, reduced isoalpha acid, tetrahydroisoalpha acid, hexa-hydroisoalpha acid, beta acid, or spent hops per day. More preferably, an effective daily dose of preferred compositions would be formulated to deliver about 50 to 7500 mg of alpha acids, isoalpha acid, reduced isoalpha acid, tetra-hydroisoalpha acid, hexa-hydroisoalpha acid, beta acid, or spent hops per day. Preferably, the effective daily dose is administered once or twice a day. A certain embodiment provides a composition comprising about 0.5 to 500 mg of isoalpha acid or reduced isoalpha acid, more preferably about 50 to 300 mg of isoalpha acid or reduced isoalpha acid per day. Another certain embodiment provides a composition comprising about 10 to 3000 mg of reduced isoalpha acid, tetra-hydroisoalpha acid, or hexa-hydroisoalpha acid per day, more preferably out 50 to 2000 mg of reduced isoalpha acid, tetra-hydroisoalpha acid, or hexahydroisoalpha acid per day. Yet another certain embodiment provides a composition comprising about 50 to 7500 mg of spent hops per day, preferably about 100 to 6000 mg of spent hops, per day.

A composition of preferred embodiments for topical application would contain about 0.001 to 10 weight percent, preferably about 0.1 to 1 weight percent of a hops derivative. Preferred embodiments would produce serum concentrations in the ranges of about 0.0001 to 10 µM, preferably about 0.01 to 1 µM of a fraction isolated or derived from hops or conjugate thereof.

Applications of Preferred Compositions

As stated previously, the generally held concept (COX dogma) is that COX-1 is expressed constitutively in most tissues whereas COX-2 is the inducible enzyme triggered by pro-inflammatory stimuli including mitogens, cytokines and bacterial lipopolysaccharide (LPS) in cells in vitro and in inflamed sites in vivo. Based primarily on such differences in expression, COX-1 has been characterized as a housekeeping enzyme and is thought to be involved in maintaining physiological functions such as cytoprotection of the gastric mucosa, regulation of renal blood flow, and control of platelet aggregation. COX-2 is considered to mainly mediate inflammation, although constitutive expression is found in brain, kidney and the gastrointestinal tract. Therefore, it would be desirable to down-regulate expression of COX-2 tissue-specifically or cell-specifically. Examples of target cells include, but are not limited to, inflammatory cells, pulmonary cells, and tumor cells. Examples of nontarget cells include, but are not limited to, gastric mucosal, neural, and renal cells.

The compositions have widespread applications. Preferred compositions can be useful for treating conditions, such as cancer, autoimmune diseases, inflammatory diseases, neurological diseases. Preferred compositions are also believed to be useful for treating conditions, such as HIV-1 infections, rhinovirus infections, and cardiovascular diseases.

Preferred embodiments would be useful for, but not limited to a number of inflammatory conditions. Thus, preferred embodiments include treatment of inflammation in a subject, and treatment of other inflammation-associated disorders, such as, as an analgesic in the treatment of pain and headaches, or as an antipyretic for the treatment of fever. Additional examples of such preferred embodiments would be useful to treat arthritis, including but not limited to rheumatoid arthritis, spondyloathopathies, gouty arthritis, osteoarthritis, systemic lupus erythematosis, and juvenile arthritis. Such preferred embodiments would be useful in the treatment of manna, bronchitis, menstrual cramps, tendonitis, bursitis, and skin related conditions such as psoriasis, eczema, burns and dermatitis. Preferred embodiments also would be useful to treat gastrointestinal conditions such as inflammatory bowel disease, Crohn's disease, gastritis, irritable bowel syndrome and ulcerative colitis and for the prevention or treatment of cancer such as colorectal cancer. Preferred embodiments would be useful in treating inflation in such diseases as vascular diseases, migraine headaches, periarteritis nodosa, thyroiditis, aplastic anemia, Hodgkin's disease, sclerodma, rheumatic fever, type 1 diabetes, myasthenia gravis, multiple sclerosis, sacoidosis, nephrotic syndrome, Behchet's syndrome, polymyositis, gingivitis, hypersensitivity, swelling occurring after injury, myocardial ischemia and the like.

Preferred embodiments would also be useful in the treatment of ophthalmic diseases, such as retinopathies, conjunctivitis, uveitis, ocular photophobia, and of acute injury to the eye tissue. Preferred embodiments would also be useful in the treatment of pulmonary inflammation, such as that associated with viral infections and cystic fibrosis. Preferred embodiments would also be useful in the treatment of asthma. Preferred embodiments would also be useful for the treatment of certain nervous system disorders such as cortical dementias including Alzheimer's disease. Preferred embodiments are useful as anti-inflammatory agents, such as for the treatment of arthritis, with the additional benefit of having significantly less harmful side effects. As inhibitors of COX-2 mediated biosynthesis of $PGE_2$, these compositions would also be useful in the treatment of allergic rhinitis, respiratory distress syndrome, endotoxin shock syndrome, atherosclerosis, and central nervous system damage resulting from stroke, ischemia and trauma. The preferred embodiments would also be useful for the treatment of fibromyalgia.

Since COX-2 can also play a role in the regulation of osteoblastic function, preferred embodiments can also be useful for treating and preventing osteoporosis. Kanematsu et al. (J Bone Miner Res 1997 November; 12(11):1789-96.) discloses that interleukin 1 (IL-1) and or necrosis factor alpha (TNF-alpha) have been implicated in the pathogenesis of osteoporosis. These proinflammatory cytokines induce both COX-2 and nitric oxide synthase (iNOS) with the release of $PGE_2$ and NO, respectively. They determined the interaction between COX and NOS pathways and their role in the regulation of osteoblastic function in MC3T3-E1 cells.

According to preferred embodiments, the animal may be a member selected from the group consisting of humans, non-human primates, dogs, cats, birds, horses, ruminants or other warm blooded animals. Preferred embodiments are directed primarily to the treatment of human beings. Administration can be by any method available to the skilled artisan, for example, by oral, topical, transdermal, transmucosal, or parenteral routes.

Besides being useful for human treatment, preferred embodiments are also useful for treatment of other animals, including horses, dogs, cats, birds, sheep, pigs, etc. A certain formulation for the treatment of inflammation would inhibit the induction and activity of COX-2 with little effect on the synthesis of $PGE_2$ in the gastric mucosa. Historically, the NSAIDs used for treatment of inflammation lacked the specificity of inhibiting COX-2 without affecting $PGE_2$ synthesis in gastric mucosal cells. Therefore, these drugs irritated and damaged the gastrointestinal system when used for extended periods.

Formulations

Preferred compositions can be administered in the form of a dietary supplement or therapeutic composition. The compositions may be administered orally, topically, transdermally, transmucosally, parenterally, etc., in appropriate dosage units, as desired.

Preferred compositions for dietary application may include various additives such as other natural components of intermediary metabolism, vitamins and minerals, as well as inert ingredients such as talc and magnesium stearate that are standard excipients in the manufacture of tablets and capsules. For example, one embodiment comprises active ingredients of preferred compositions in combination with glucosamine or chondrotin sulfate.

As used herein, "pharmaceutically acceptable carrier" includes any and all solvents, dispersion media, coatings, isotonic and absorption delaying agents, sweeteners and the like. These pharmaceutically acceptable carriers may be prepared from a wide range of materials including, but not limited to, diluents, binders and adhesives, lubricants, disintegrants, coloring agents, bulking agents, flavoring agents, sweetening agents and miscellaneous materials such as buffers and absorbents that may be needed in order to prepare a particular therapeutic composition. The use of such media and agents for pharmaceutically active substances is well known in the art. Except insofar as any conventional media or agent is incompatible with the active ingredients, its use in preferred compositions is contemplated. In one embodiment, talc, and magnesium stearate are included in the formulation. Other ingredients known to affect the manufacture of this composition as a dietary bar or functional food can include flavorings, sugars, amino-sugars, proteins and/or modified starches, as well as fats and oils.

Dietary supplements, lotions or therapeutic compositions of preferred embodiments can be formulated in any manner known by one of skill in the art. In one embodiment, the composition is formulated into a capsule or tablet using techniques available to one of skill in the art. In capsule or tablet form, the recommended daily dose for an adult human or animal would preferably be contained in one to six capsules or tablets. However, preferred compositions can also be formulated in other convenient forms, such as an injectable solution or suspension, a spray solution or suspension, a lotion, gum, lozenge, food or snack item. Food, snack, gum or lozenge items can include any ingestible ingredient, including sweeteners, flavorings, oils, starches, proteins, fruits or fruit extracts, vegetables or vegetable extracts, grains, animal fats or proteins. Thus, preferred compositions can be formulated into cereals, snack items such as chips, bars, gumdrops, chewable candies or slowly dissolving lozenges. Preferred embodiments contemplate treatment of all types of inflammation-based diseases, both acute and chronic. Preferred formulations reduce the inflammatory response and thereby promotes healing of, or prevents further damage to, the affected tissue. A pharmaceutically acceptable carrier can also be used in the preferred compositions and formulations.

Assay Using AGS Cell Line

The Kuhns patent application referenced previously attempts to identify therapeutic components based on the Modified Whole Blood/Cell Assay of T. D. Warner et al., *Nonsteroid drug selectivities for cyclooxygenase-1 rather than cyclooxygenase-2 are associated with human gastrointestinal toxicity: A full in vitro analysis*, Proc. Natl. Sci. USA 96:7563-68 (1999) in paragraph [0046]. When tested according to this procedure, hops extracts do not yield $IC_{50}$ values in the necessary µg/mL range, since they are not direct inhibitors of COX-2. This lack of direct inhibition of COX-2 was demonstrated by Tobe, H. et al. 1997. (*Bone resorption inhibitors from hop extract*. Biosci. Biotech. Biochem 61(1) 158-159) using purified COX-2 enzyme. Similarly, Example 4 of this application demonstrates that, when tested according to the Modified Whole Blood/Cell Assay, hops compounds and derivatives produce median inhibitory concentrations greater than 25 µg/mL. Such high median inhibitory concentrations are pharmacologically unsuitable. Therefore, the Modified Whole Blood Assay as described by Warner is an invalid procedure for formulating potentially therapeutically effective combinations containing hops or hops derivatives.

The discovery of COX-2 has made possible the design of drugs that reduce inflammation without removing the protective PGs in the stomach and kidney made by COX-1. One of our approaches is to screen compositions of the preferred embodiments using in vitro animal cells to assess COX-2 and COX-1 inhibitory activity employing $PGE_2$, which has cytoprotective actions and play a role in maintaining the integrity of the gastrointestinal mucosa, as an endpoint. Secondarily, different cell types are used to confirm results. The screening process would indicate compositions that have specific COX-2 activity and limited COX-1 inhibition. Compositions of preferred embodiments can be tested in two cell types: 1) human pulmonary cells or other cell line to determine and identify optimal amounts and ratios for compositions comprising more than one component; and 2) human gastric epithelial cells (AGS cell line), a gastrointestinal tract cell line and a model system for assessing toxicity which is typically related to inhibition of COX-1 which is required for wound healing (such as ulcers). Hence, compositions of preferred embodiments that can inhibit COX-2 or COX-2 induction can be screened by selecting compositions that have low or no activity in AGS cells and good activity in human pulmonary cells or other cell line.

The description below is of specific examples setting forth preferred embodiments and are not intended to limit the scope.

Example 1

AGS Gastric Mucosal Cells Constitutively Express Both Cyclooxygenase-1 and Cyclooxygenase-2

Summary—This example demonstrates that the AGS human gastric mucosal cell line, possessing constitutive expression of COX-1 and COX-2, has excellent potential to serve as a model for assessing the gastrointestinal toxicity of cyclooxygenase-inhibiting compounds.

Equipment used in this example included: an OHAS Model #E01140 analytical balance, a Form a Model #F1214 biosafety cabinet (Marietta, Ohio), various pipettes to deliver 0.1 to 100 µL, (VWR, Rochester, N.Y.), a cell hand tally counter (VWR. Catalog #23609-102, Rochester, N.Y.), a Form a Model #F3210 $CO_2$ incubator (Marietta, Ohio), a hemacytometer (Hausser Model #1492, Horsham, Pa.), a Leica Model #DM IL inverted microscope (Wetzlar, Germany), a PURELAB Plus Water Polishing System (U.S. Filter, Lowell, Mass.), a 4° C. refrigerator (Form a Model #F3775, Marietta, Ohio), a vortex mixer (VWR Catalog #33994-306, Rochester, N.Y.), and a 37° C. water bath (Shel Lab Model #1203, Cornelius, Oreg.).

Chemicals and reagents—Prostaglandin $E_2$ EIA kit Monoclonal was purchased from Cayman Chemical (Ann Arbor. W. Anti-COX-1 and anti-COX-2 rabbit polyclonal antisera were obtained from Upstate Biotechnology (CITY, NY); donkey anti-goat IgG-HRP was procured from Santa Cruz Biotechnology (City, Calif.). Heat inactivated Fetal Bovine Serum (FBS-HI Cat. #35-011CV), and Dulbeco's Modification of Eagle's Medium (DMEM Cat #10-013CV) was purchased from Mediatech (Herndon, Va.). All standard reagents were obtained from Sigma (St. Louis, Mo.) and were the purest commercially available.

Cell Culture—The human gastric mucosal cell line AGS was obtained from the American Type Culture Collection (Manassas, Va.) and sub-cultured according to the instructions of the supplier. The cells were routinely cultured at 37° C. with 5% $CO_2$ in RPMI 1640 containing 10% FBS, with 50 units penicillin/mL 50 µg streptomycin/mL, 5% sodium pyruvate, and 5% L-glutamine. Exponentially growing cells were seeded into 6-well plates and grown to confluence. A 20 µL aliquot of the supernatant media was sampled for determination of $PGE_2$ content. Cells were then washed in PBS, scraped and lysed for immunoblotting.

Protein assay—Protein concentrations of cell lysates were determined using the NanoOrange Protein Quantitation Kit with bovine serum albumin as the standard (Molecular Probes, Eugene, OE) according to the procedure supplied by the manufacturer. Fluorescence was determined using a Packard FluoroCount, Model BF 10000 fluorometer with the excitation filter set at 485 nm and emission filter set at 570 nm using Packard PlateReader version 3.0 software. The I-Smart program provided with the Packard PlateReader was used to calculate the protein concentration.

Immunoblotting—Western blotting of COX-1 and COX-2 was performed using PAGEr™ Gold Precast Gels (Bio Whittaker Molecular Applications (Rockland, Me.). AGS cell lysates containing approximately 60 µg protein were loaded with Laemmli Sample Buffer into the wells of the gel in a total volume of 30 µL. The vertical minigel electrophoresis chambers were made by Savant Instruments Inc. (Holbrook, N.Y.), model MV 120. Gels were run at 40 mA/plate (constant current) at room temperature until the bromophenol blue stain reached the bottom of the gel, about one h. Gels were then blotted on the polyvinyl fluoride transfer membranes (Pall Corporation, Ann Arbor, Mich.), overnight, at 500 mA and 4° C. Precision Protein Standard molecular weight markers, unstained, broad range (BioRad, Hercules, Calif.) were used. The BioWest™ Extended duration chemiluminescent substrate, a non-isotopic, horseradish peroxidase substrate kit for Western blot detection (BioImaging Systems, Upland, Calif.) was used for protein visualization. Images of western blots were acquired using a UVP Epi Chemi II Darkroom (BioImaging Systems), analyzed and enhanced by LabWorks™ Image Acquisition and Analysis Software (BioImaging Systems).

$PGE_2$ assay—A commercial, non-radioactive procedure for quantification of $PGE_2$ was employed (Caymen Chemical, Ann Arbor, Mich.) and the recommended procedure of the manufacturer was used without modification. Briefly, 25 µL of the medium, along with a serial dilution of $PGE_2$ standard samples, were mixed with appropriate amounts of acetylcholinesterase-labeled tracer and PGE, antiserum, and incubated at room temperature for 18 h. After the wells were emptied and rinsed with wash buffer, 200 µL of Ellman's reagent containing substrate for acetylcholinesterase were added. The reaction was carried out on a slow shaker at room temperature for 1 h and the absorbance at 415 nm was determined. The $PGE_2$ concentration was represented as picograms per $10^5$ cells.

Figure 4:
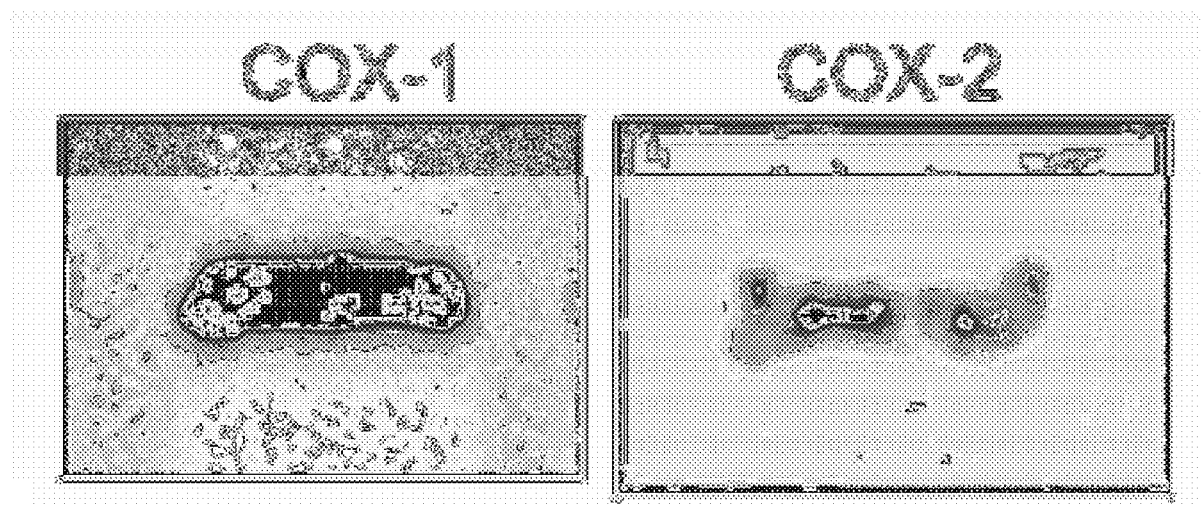
FIG. 4 are representative immunoblots demonstrating constitutive COX-1 and COX-2 expression in AGS human gastric mucosal cells. The AGS human gastric cell line was cultured in 6-well plates at 37° C. with 5% $CO_2$ in a humidified incubator for 24 hours. Cells were lysed on ice in lysis buffer and protein concentration determined. Fifty μg of cell lysate were solubilized, fractionated on a 10% polyacrylamide gel containing sodium dodecylsulfate (SDS), and transferred onto a nitrocellulose membrane. The membranes were incubated in a blocking buffer and then incubated with the respective primary antibody for 1 h at room temperature. Following primary antibody incubation, the blots were washed three times with Tris-buffered saline and then incubated with the secondary antibody for 1 h. Protein bands were visualized using enhanced chemiluminescence.

Results—As seen in FIG. 4, the AGS cell line constitutively expresses both COX-1 and COX-2, with COX-1 expression approximately 4-times greater than COX-2 expression. $PGE_2$ synthesis in AGS cells over 18 h was 660 pg/$10^5$ cells. Thus, this example demonstrates that the AGS human gastric mucosal cell line, possessing constitutive expression of COX-1 and COX-2, has excellent potential to serve as a model for assessing the gastrointestinal toxicity of cyclooxygenase-inhibiting compounds.

In the past, the classical COX-2 hypothesis has downplayed the role of COX-2 expression in the gastrointestinal mucosa. While in normal gastric mucosa COX-1 is the predominant COX isozyme, as demonstrated in this example and in the literature, there is increasing evidence that detectable amount of COX-2 mRNA and protein are both constitutively expressed and inducible in specific locations of the gastric mucosa in both animals and humans [Halter, F., et al. (2001) *Cyclooxygenase 2-implications on maintenance of gastric mucosal integrity and ulcer healing: controversial issues and perspectives*. Gut 49, 443-453]. Recent studies in rats have shown that whereas selective inhibition of COX-1 or COX-2 is not ulcerogenic, combined inhibition of both COX-1 and COX-2 induces severe lesions in the stomach and small intestine comparable with the effects of NSAID such as indomethacin. This observation suggests an important contribution of COX-2 to the maintenance of gastrointestinal mucosal integrity.

Example 2

Inhibition of $PGE_2$ Synthesis in Gastric Mucosal Cells by Nunsteroidal Anti-Inflammatory Drugs Summary—This example illustrates that inhibition of $PGE_2$ synthesis in AGS gastric cells by NSAIDs correlates with their observed clinical gastric irritation.

Chemicals—Rofecoxib and celexocib were obtained. Diisofluorophosphate (DIFP), nimensulide, ibuprofen, salicylic acid, aspirin, indomethacin and acetaminophen were purchased from Sigma (St. Louis, Mo.). All other chemicals were obtained from suppliers as described in Example 1.

Cells—A549 (human pulmonary epithelial) and AGS cells (human gastric mucosa) were obtained from the American Type Culture Collection (Manassas, Va.) and sub-cultured according to the instructions of the supplier. The cells were routinely cultured at 37° C. with 5% $CO_2$ in RPMI 1640 containing 10% FBS, with 50 units penicillin/ml, 50 μg streptomycin/mL, 5% sodium pyruvate, and 5% L-glutamine. On the day of the experiments, exponentially growing cells were harvested and washed with serum-free RPMI 1640.

The log phase A549 and AGS cells were plated at $8 \times 10^4$ cells per well in 0.2 mL growth medium per well in a 96-well tissue culture plate. For the determination of $PGE_2$ inhibition by the test compounds in A549 cells, the procedure of Warner et al., also known as the WHMA-COX-2 protocol [Warner, T. D., et al. (1999) *Nonsteroid drug selectivities for cyclo-oxygenise-1 rather than cyclo-oxygenise-2 are associated with human gastrointestinal toxicity: a full in vitro analysis*. Proc Natl Acad Sci USA 96, 7563-7568] was followed with no modifications. Briefly, 24 hours after plating of the A549 cells, interleukin-1β (10 ng/mL) was added to induce the expression of COX-2. After 24 hr, the cells were washed with serum-free RPMI 1640 and the test materials, dissolved in DMSO and serum-free RPMI, were added to the wells to achieve final concentrations of 25, 5.0, 0.5 and 0.05 μg/mL. Each concentration was run in duplicate. DMSO was added to the control wells in an equal volume to that contained in the test wells. Sixty minutes later, A23187 (50 μM) was added to the wells to release arachidonic acid. Twenty-five μL of media were sampled from the wells 30 minutes later for $PGE_2$ determination.

Non-stimulated AGS cells were used in these studies. Twenty-four hours after plating in the 96-well microtiter plates, the cells were washed with serum-free RPMI 1640 and the test materials, dissolved in DMSO and serum-free RPMI, were added to the wells to achieve final concentrations of 25, 5.0, 0.5 and 0.05 μg/mL. Each concentration was run in duplicate. DMSO was added to the control wells in an equal volume to that contained in the test wells. Sixty minutes later, arachidonic acid was added to the wells to achieve a final concentration of 100 μM. Twenty-five μL of media were sampled from the wells 30 minutes after the addition of arachidonic acid for $PGE_2$ determination.

Cell viability—Cell viability was assessed by a 3-(4,5-dimethylthiazol-2-yl)-2,5-diphenyltetrazolium bromide (MTT)-based colorimetric assay (Sigma, St. Louis, Mo.). The Mn solution was added directly to the wells after sampling for $PGE_2$ determination. The absorbance of each well was read at 580 nm using an ELISA plate reader. No toxicity was observed at the highest concentrations tested for any of the compounds, Calculations—The median inhibitory concentration ($IC_{50}$) for $PGE_2$ synthesis was calculated using CalcuSyn (BIO-SOFT. Ferguson, Mo.). This statistical package performs multiple drug dose-effect calculations using the median effect methods described by T-C Chou and P. Talaly [(1984) *Quantitative analysis of dose-effect relationships: the combined effects of multiple drugs or enzyme inhibitors*. Adv Enzyme Regal 22, 27-55.] hereby incorporated by reference.

Briefly, the analysis correlates the "Dose" and the "Effect" in the simplest possible form: $fa/fu=(C/C_m)^m$, where C is the concentration or dose of the compound and Cm is the median-effective dose signifying the potency. Cm is determined from the x-intercept of the median-effect plot. The fraction affected by the concentration of the test material is fa and the fraction unaffected by the concentration is fu(fu=1−fa). The exponent m is the parameter signifying the sigmoidicity or shape of the dose-effect curve. It is estimated by the slope of the median-effect plot.

The median-effect plot is a graph of x=log(C) vs y=log(fa/fu) and is based on the logarithmic form of Chou's median-effect equation. The goodness of fit for the data to the median-effect equation is represented by the linear correlation coefficient r of the median-effect plot. Usually, the experimental data from enzyme or receptor systems have an r>0.96, from tissue culture an r>0.90 and from animal systems an r>0.85. In the cell-based studies reported here, all linear correlation coefficients were greater than 0.90. Experiments were repeated three times on three different dates. The percent inhibition at each dose was averaged over the three independent experiments and used to calculate the median inhibitory concentrations reported.

Results—The highly specific COX-2 inhibitor diisofluorophosphate exhibited a median inhibitory concentration in A549 cells of 1.19 μg/mL and did not inhibit $PGE_2$ synthesis in AGS cells at the highest concentration tested of 25 μg/mL (Table 3). Rofecoxib, and celexocib, selective COX-2 drugs, were 27-, and 14-times, respectively, more potent inhibitors of $PGE_2$ synthesis in the target A549 cells than in the non-target AGS gastric mucosal cells. This finding demonstrates not only COX-2 selectivity, but also target-tissue selectivity consistent with their low gastrointestinal toxicity. Nimensulide, another new, selective COX-2 inhibitor was equally as potent in the inhibition of $PGE_2$ synthesis in both cell lines. The anti-inflammatory agent acetaminophen, purported to inhibit an unidentified isozyme of COX(COX-3) and having low gastrointestinal toxicity, inhibited $PGE_2$ biosynthesis in A549 cells but had no effect on $PGE_2$ synthesis in AGS gastric mucosal cells.

Alternatively and consistent with their demonstrated clinical gastric toxicity, ibuprofen, aspirin and indomethacin all exhibited more inhibition of $PGE_2$ synthesis in the AGS cell line than in the target A549 cells. Salicylic acid, an anti-inflammatory agent that inhibits the expression of COX-2 with little gastric irritation, was inactive in both cell models.

TABLE 3

Median inhibitory concentrations for test compounds in the A549 and AGS cell lines.

| Compound | $IC_{50}$ A549 [μg/mL] | $IC_{50}$ AGS [μg/mL] | $IC_{50}$AGS/ $IC_{50}$ A549 |
|---|---|---|---|
| Diisouorophosphate | 1.19 | >25 | >21 |
| Rofecoxib | 0.081 | 2.21 | 27.3 |
| Celxocib | 0.004 | 0.055 | 13.8 |
| Nimensulide | 0.10 | 0.11 | 1.0 |
| Ibuprofen | 0.10 | 0.05 | 0.50 |
| Aspirin | 0.48 | 0.09 | 0.19 |
| Indomethacin | 0.033 | 0.002 | 0.002 |

TABLE 3-continued

Median inhibitory concentrations for test compounds in the
A549 and AGS cell lines.

| Compound | $IC_{50}$ A549 [μg/mL] | $IC_{50}$ AGS [μg/mL] | $IC_{50}$ AGS/ $IC_{50}$ A549 |
|---|---|---|---|
| Salicylic acid | >25 | >25 | >1 |
| Acetaminophen | 0.607 | >25 | >41 |

These results validate the use of the AGS gastric mucosal cell line to evaluate potential gastrointestinal toxicity of anti-inflammatory agents capable of inhibiting the synthesis of $PGE_2$. They also demonstrate cellular specificity in the action of COX-inhibiting compounds. A ratio of I for $IC_{50}$ AGS/$IC_{50}$ A549 indicates $IC_{50}$'s that are the same for both the AGS cell and A549 cells. If the ratio is higher than 1 for $IC_{50}$ AGS/$IC_{50}$ A549, then the inhibition of $PGE_2$ is lower for the AGS cells. A lower inhibition of $PGE_2$ in AGS cells is favorable because AGS cell line expresses more COX-1, which maintains mucosal homeostasis.

Example 3

Inhibition of $PGE_2$ Synthesis in Stimulated and Nonstimulated Murine Macrophages by Hops (*Humulus lupulus*) Compounds and Derviatives Summary—This example illustrates the potency of hops fractions and derivatives to inhibit COX-2 synthesis of $PGE_2$ preferentially over COX-1 synthesis of $PGE_2$ in the murine macrophage model.

Chemicals and reagents—Bacterial lipopolysaccharide (LPS; B *E. coli* 055:B5) was from Sigma (St. Louis, Mo.). Hops fractions (1) alpha hop (1% alpha acids; AA), (2) aromahop OE (10% beta acids and 2% isomerized alpha acids, (3) isohop (isomerized alpha acids; IAA). (4) beta acid solution (beta acids BA), (5) hexahop gold (hexahydro isomerized alpha acids; HHIAA), (6) redihop (reduced isomerized-alpha acids; RIAA), (7) tetrahop (tetrahydro-iso-alpha acids THIAA) and (8) spent hops were obtained from Betatech Hops Products (Washington, D.C., U.S.A.). The spent hops were extracted two times with equal volumes of absolute ethanol. The ethanol was removed by heating at 40° C. until a only thick brown residue remained. This residue was dissolved in DMSO for testing in RAW 264.7 cells. Unless otherwise noted, all standard reagents were obtained from Sigma (St. Louis, Mo.) and were the purest commercially available. All other chemicals and equipment were as described in Examples 1 and 2.

Cell culture—RAW 264.7 cells, obtained from American Type Culture Collection (Catalog #TIB-71, Manassas, Va.), were grown in Dulbecco's Modification of Eagle's Medium (DMEM, Mediatech, Herndon, Va.) and maintained in log phase. The DMEM growth medium was made by adding 50 mL of heat inactivated FBS and 5 mL of penicillin/streptomycin to a 500 mL bottle of DMEM and storing at 4° C. The growth medium was warmed to 37° C. in water bath before use.

On day one of the experiment, the log phase RAW 264.7 cells were plated at $8 \times 10^4$ cells per well in 0.2 mL growth medium per well in a 96-well tissue culture plate in the morning. At the end of the day one (6 to 8 h post plating), 100 μL, of growth medium from each well were removed and replaced with 100 μL fresh medium.

A 1.0 mg/mL stock solution of LPS, used to induce the expression of COX-2 in the RAW 264.7 cells, was prepared by dissolving 1.0 mg of LPS in 1 mL DMSO. It was vortexed until dissolved and stored at 4° C. Before use, it was melted at room temperature or in a 37° C. water bath.

On day two of the experiment, test materials were prepared as 1000× stock in DMSO. In 1.7 mL microfuge tubes, 1 mL DMEM without FBS was added for test concentrations of 0.05, 0.10, 0.5, and 1.0 μg/mL. Two μL of the 1000×DMSO stock of the test material was added to the 1 mL of medium without FBS. The tube contained the final concentration of the test material concentrated 2-fold and placed tube in an incubator for 10 minutes to equilibrate to 37° C.

For COX-2 associated PGE2 synthesis, 100 μL of medium were removed from each well of the cell plates prepared on day one and replaced with 100 μL of equilibrated 2× final concentration of the test compounds. Cells were then incubated for 90 minutes. Twenty μL of LPS were added to each well of cells to be stimulated to achieve a final concentration of 1 μg LPS/ml., and the cells were incubated for 4 h. The cells were further incubated with 5 μM arachidonic acid for 15 minutes. Twenty-five μL of supernatant medium from each well was transferred to a clean microfuge tube for the determination of $PGE_2$ released into the medium.

Following the LPS stimulation, the appearance of the cells was observed and viability was determined as described in Example 2. No toxicity was observed at the highest concentrations tested for any of the compounds. Twenty-five μL of supernatant medium from each well was transferred to a clean microfuge tube for the determination of $PGE_2$ released into the medium. $PGE_2$ was determined and reported as previously described in Example 1.

For COX-1 associated $PGE_2$ synthesis, 100 μL of medium were removed from each well of the cell plates prepared on day one and replaced with 100 μL of equilibrated 2× final concentration of the test compounds. Cells were then incubated for 90 minutes. Next, instead of LPS stimulation, the cells were incubated with 100 μM arachidonic acid for 15 minutes. Twenty-five μL of supernatant medium from each well was transferred to a clean microfuge tube for the determination of $PGE_2$ released into the medium.

The appearance of the cells was observed and viability was determined as described in Example 2. No toxicity was observed at the highest concentrations tested for any of the compounds. Twenty-five μL of supernatant medium from each well was transferred to a clean microfuge tube for the determination of $PGE_2$ released into the medium. $PGE_2$ was determined and reported as previously described in Example 1. The median inhibitory concentrations ($IC_{50}$) for $PGE_2$ synthesis from both COX-2 and COX-1 were calculated as described in Example 2.

TABLE 4

COX-2 and COX-1 inhibition in RAW 264.7 cells by hop fractions and derivatives

| Test Material | COS-2 IC50 [μg/mL] | COX-1 $IC_{50}$ [μg/mL] | COX-1/ COX-2 |
|---|---|---|---|
| Alpha hop (AA) | 0.21 | 6.2 | 30 |
| Aromahop OE | 1.6 | 4.1 | 2.6 |
| isohop (IAA) | 0.13 | 18 | 144 |
| Beta acids (BA) | 0.54 | 29 | 54 |
| Hexahop (FIHIAA) | 0.29 | 3.0 | 11 |
| Redihop (RIAA) | 0.34 | 29 | 87 |
| Tetrahop (THIAA) | 0.20 | 4.0 | 21 |
| Spent hops (EtOH) | 0.88 | 21 | 24 |

As seen in Table 4, all hops fractions and derivative selectively inhibited COX-2 over COX-1 in this target macrophage model. This was a novel and unexpected finding. The extent of COX-2 selectivity for the hops derivatives IAA and RIAA, respectively, 144- and 87-fold, was unanticipated. Such high COX-2 selectivity combined with low median inhibitory concentrations, has not been previously reported for natural products from other sources.

Example 4

Hops Compounds and Derivatives are not Direct Cyclooxygenase Enzyme Inhibitors

Summary—This example illustrates that hops compounds and derivatives do not inhibit PGE, synthesis in A549 pulmonary epithelial cells at physiologically relevant concentrations when tested using the VVHMA-COX-2 protocol.

Chemicals—Hops and hops derivatives used in this example were previously described in Example 3. All other chemicals were obtained from suppliers as described in Examples 1 and 2.

Cells—A549 (human pulmonary epithelial) Cells were obtained from the American Type Culture Collection (Manassas, Va.) and sub-cultured according to the instructions of the supplier. The cells were routinely cultured at 37° C. with 5% $CO_2$ in RPMI 1640 containing 10% FBS, with 50 units penicillin/mL, 50 gg streptomycin/mL, 5% sodium pyruvate, and 5% L-glutamine. On the day of the experiments, exponentially growing cells were harvested and washed with serum-free RPMI 1640.

Log phase A549 cells were plated at $8\times10^4$ cells per well with 0.2 mL growth medium per well in a 96-well tissue culture plate. For the determination of $PGE_2$ inhibition by the test compounds, the procedure of Warner et al. [(1999) *Non-steroid drug selectivities for cyclo-oxygenase-1 rather than cyclo-oxygenase-2 are associated with human gastrointestinal toxicity: a full in vitro analysis*. Proc Natl Acad Sci USA 96, 7563-7568], also known as the WHIM-COX-2 protocol was followed with no modification. Briefly, 24 hours after plating of the A549 cells, interleukin-113 (10 ng/mL) was added to induce the expression of After 24 hr, the cells were washed with serum-free RPMI 1640 and the test materials, dissolved in DMSO and serum-free RPMI, were added to the wells to achieve final concentrations of 25, 5.0, 0.5 and 0.05 µg/. Each concentration was run in duplicate. DMSO was added to the control wells in an equal volume to that contained in the test wells. Sixty minutes later, A23187 (50 µM) was added to the wells to release arachidonic acid. Twenty-five µL of media were sampled from the wells 30 minutes later for $PGE_2$ determination.

Cell viability was assessed as previously described in Example 2. No toxicity was observed at the highest concentrations tested for any of the compounds. $PGE_2$ in the supernatant medium was determined and reported as previously described in Example 1.

The median inhibitory concentration ($IC_{50}$) for $PGE_2$ synthesis was calculated as previously described in Example 2.

Results—At the doses tested, the experimental protocol failed to capture a median effective concentration of any of the hops extracts or derivatives. Since the protocol requires the stimulation of COX-2 expression prior to the addition of the test compounds, the likely answer to the failure of the test materials to inhibit $PGE_2$ synthesis is that their mechanism of action is to inhibit the expression of the COX-2 isozyme and not activity directly. While some direct inhibition can be observed using the VVHMA-COX-2 protocol, this procedure is inappropriate in evaluating the anti-inflammatory properties of hops compounds or derivatives of hops compounds.

Example 5

Lack of Inhibition of $PGE_2$ Synthesis in Gastric Mucosal Cells by Hops (*Humulus lupulus*) Compounds and Derviatives Summary—This example illustrates the lack of $PGE_2$ inhibition by hops fractions and in the AGS human gastric mucosal cell line implying low gastric irritancy potential of these compounds.

Chemicals and reagents were used as described in Example 3. AGS cells were grown and used for testing hops compounds and derivatives as described in Example 2. $PGE_2$ was determined and reported as previously described in Example 1. The median inhibitory concentrations ($IC_{50}$) for $PGE_2$ synthesis from AGS cells were calculated as described in Example 2.

TABLE 5

Lack of $PGE_2$ inhibition in AGS gastric mucosal cells by hop fractions and derivatives

| Test Material | IC50 AGS [µg/mL] |
|---|---|
| Alpha hop (AA) | >25 |
| Aromahop OE | >25 |
| Isohop (IAA) | >25 |
| Beta acids (BA) | >25 |
| Hexahop (HHIAA) | >25 |
| R.edihop (R.IAA) | >25 |
| Tetrahop (THIAA) | >25 |
| Spent hops (EtOH) | >25 |

As seen in Table 5, all hops fractions and derivatives were unable to were unable to inhibit $PGE_2$ synthesis by 50% or more at the highest concentrations tested in the AGS gastric mucosal cell line. Based on the anti-inflammatory potency exhibited by these fractions in target macrophages, this was a novel and unexpected finding.

Example 6

Normalization of Joint Function Following Trauma

A representative composition of the preferred embodiments as a dietary supplement would be in an oral formulation, i.e. tablets or gel caps that would supply one of the following combinations: 0.1 to 10 mg isocohumulone/kg per day; 0.01 to 10 mg dihydro-isoadhumulone/kg per day; 0.01 to 10 mg tetrahydro-isocohumulone/kg per day; 0.01 to 10 mg/kg per day of hexahydro-isohumulone/kg per day for a 70 kg person.

Normalization of joint movement following physical trauma due to exercise or repetitive movement stress would be expected to occur following two to ten doses. This result would be expected in all animals.

Example 7

Clinical Effectiveness of Lotion Formulations in the Treatment of Acne Rosacea

A lotion designed to contain one of the following:
1. 0.1% wt of the isomerized alpha-acid isocohumulone;

2. 0.1% wt of the reduced isomerized alpha-acid dihydro-isoadhumulone;
3. 0.1% wt of the tetrahydroisoalpha-acid tetrahydro-isocohumulone; or
4. 0.1% wt hexahydro-isohumulone is applied to affected areas of patients who have exhibited acne rosacea as diagnosed by their health practitioner and confirmed by an independent board-certified dermatologist.

Self-evaluation tests and are administered one week prior to the study to quantify the surface area affected and redness. In addition, similar variables are scored by the professional clinical staff not aware of the patients treatment status. These evaluations are repeated on Days 0, 7, 14 and 21.

Patients are randomly assigned to the test formulation or placebo at the start of the study. The test formulation and placebo are applied to the affected area one or two times per day. Treatment for health conditions such as diabetes, hypertension, etc. is allowed during the study. Scores are statistically compared between the test formulation and the placebo for each of the four observational periods. Patients treated with the composition of the preferred embodiments in a lotion formulation are considered improved if the patients' scores improve by greater than 20% from the pre-test scores within each category evaluated. The percentage of persons exhibiting improvement is compared between the combination formulations and the placebo control. The difference between the two groups is considered statistically significant if the probability of rejecting the null hypothesis when true is less than five percent.

Example 8

Clinical Effectiveness of a Lotion Formulation in the Treatment Of Psoriasis

This example is performed in the same manner as described in Example 7, except that the composition is applied to affected areas of patients who have exhibited psoriasis as diagnosed by their own practitioner and confirmed by an independent board-certified dermatologist. Self-evaluation tests are administered one week prior to the study to quantify the surface area affected and skin condition. In addition, similar variables are scored by the professional clinical staff not aware of the patients treatment status. These evaluations are repeated on Days 0, 7, 30 and 60.

Patients are randomly assigned to the test formulation or placebo at the start of the study. The test formulation and placebo are applied to the affected area one or two times per day. Treatment for health conditions such as diabetes, hypertension, etc. is allowed during the study. Scores are statistically compared between the test formulation and the placebo for each of the four observational periods. Patients treated with the composition of the preferred embodiments as the test lotion formulation are considered improved if the patients' scores improve by greater than 20% from the pre-test scores within each category evaluated. The percentage of persons exhibiting improvement is compared between the test formulation and the placebo control. The difference between the two groups is considered statistically significant if the probability of rejecting the null hypothesis when true is less than five percent.

Example 9

Clinical Effectiveness of a Formulation in the Treatment of Alzheimer's Disease

An oral formulation as described in Example 6 is administered to patients who have manifested an early stage of Alzheimer's Disease (AD), as diagnosed by their practitioner and confirmed by an independent board-certified neurologist. Two weeks before the clinical trial, the patients undergo appropriate psychoneurological tests such as the Mini Mental Status Exam (MMSE), the Alzheimer Disease Assessment Scale (ADAS), the Boston Naming Test (BNT), and the Token Test (TT). Neuropsychological tests are repeated on Day 0, 6 weeks and 3 months of the clinical trial. The tests are performed by neuropsychologists who are not aware of the patient's treatment regimen.

Patients are randomly assigned to the test formulation or placebo at the start of the study. The test formulation and placebo are taken orally one or two times per day. Treatment for conditions such as diabetes, hypertension, etc. is allowed during the study. Scores are statistically compared between the test formulation and the placebo for each of the three observational periods. Without treatment, the natural course of AD is significant deterioration in the test scores during the course of the clinical trial. Patients treated with the composition of the preferred embodiments as the test formulation are considered improved if the patients' scores remain the same or improve during the course of the clinical trial.

Example 10

Oral Formulation in the Treatment and Prevention of Colon Cancer

An oral formulation as described in Example 6 is administered to patients who have manifested an early stage of colon cancer as diagnosed by their own practitioner and confirmed by a independent board-certified oncologist.

Patients are randomly assigned to the test formulation or a placebo at the start of the study. The test formulation and placebo are taken orally one or two times per day. Treatment for conditions such as diabetes, hypertension. etc. is allowed during the study. Endoscopic evaluations are made at one, two, six and twelve months. Evidence of reappearance of the tumor during any one of the four follow-up clinical visits is considered a treatment failure. The percentage of treatment failures is compared between the test formulation and the placebo control. Under the experimental conditions described, the test material is expected to decrease the tumor incidence with respect to the control group. The difference between the two groups is considered statistically significant if the probability of rejecting the null hypothesis when true is less than five percent.

Example 11

Oral Formulation for the Treatment of Irritable Bowel Syndrome

An oral formulation as described in Example 6 is administered to patients who have manifested irritable bowel syndrome as diagnosed by their practitioner. Normal bowel functioning is restored within 48 hours.

Example 12

Normalization of Joint Functioning in Osteoarthritis

Using compositions described in Example 6 normalization of joint stiffness due to osteoarthritis occurs following five to twenty doses, in the presence or absence of glucosamine or chondroitin sulfate. In addition, the composition does not interfere with the normal joint rebuilding effects of these two proteoglycan constituents, unlike traditional non-steroidal anti-inflammatory agents.

Example 13

Mite Dust Allergens Activate PGE$_2$ Biosynthesis in A549 Pulmonary Cells

Summary—This example illustrates that house mite dust allergens can induce PGE2 biosynthesis in pulmonary epithelial cells.

Background

Sensitivity to allergens is a problem for an increasing number of consumers. This issue has been complicated by a surprising increase in asthma over the past few years. Asthma suffers are especially sensitive to airborne allergens. Allergy rates are also on the rise. This gives rise to increased awareness of the causes of allergy symptoms and how to decrease the associated discomfort. Approximately 10% of the population become hypersensitized (allergic) upon exposure to antigens from a variety of environmental sources. Those antigens that induce immediate and/or delayed types of hypersensitivity are known as allergens. These include products of grasses, trees, weeds, animal dander, insects, food, drugs, and chemicals. Genetic predisposition of an individual is believed to play a role in the development of immediate allergic responses such as atopy and anaphylaxis whose symptoms include hay fever, asthma, and hives.

Many allergens are protein-based molecules, and these protein allergens can originate from many sources. It has been known for some time that one of the most common sources of allergens in a house is from dust mites. Of course, as is the case with all allergens, only certain people are allergic to dust mite allergens. But this group of people can be quite large in many areas, especially in hot humid areas. For example, in the southeastern United States of America, where it is both hot and humid for much of the year, the incidence of house dust mite allergies in the general population can be as high as 25%. House dust mites thrive in plush carpets, overstuffed upholstery, cushy bed comforters and the like.

Methods

Mite dust allergen isolation—*Dermatophagoides farinae* are the American house dust mite. *D. farinae* were cultured on a 1:1 ratio of Purina Laboratory Chow (Ralston Purina, Co, St. Louis, Mo.) and Fleisclunann's granulated dry yeast (Standard Brands, Inc. New York, N.Y.) at room temperature and 75% humidity. Live mites were aspirated from the culture container as they migrated from the medium, killed by freezing, desiccated and stored at 0% humidity. The allergenic component of the mite dust was extracted with water at ambient temperature. Five-hundred mg of mite powder were added to 5 mL of water (1:10 w/v) in a 15 mL conical centrifuge tube (VWR, Rochester, N.Y.), shaken for one minute and allowed to stand overnight at ambient temperature. The next day, the aqueous phase was filtered using a 0.2 μm disposable syringe filter (Nalgene, Rochester, N.Y.). The filtrate was termed mite dust allergen and used to test for induction of PGE$_2$ biosynthesis in A549 pulmonary epithelial cells.

Cell culture and treatment—This experiment involved the human airway epithelial cell line, A549 (American Type Culture Collection, Bethesda, Md.). The cells were cultured and treated as previously described in Example 2. Mite allergen was added to the culture medium to achieve a final concentration of 1000 ng/mL. Twenty-four hours later, the culture medium was sampled for PGE$_2$ concentration.

PGE$_2$ assay—Determination of PGE$_2$ in the culture medium was performed as previously described in Example 1.

Statistical analysis—Means of eight replicates per treatment were computed using Excel® spreadsheets (Microsoft, Redmond, Wash.).

Results

Figure 5:
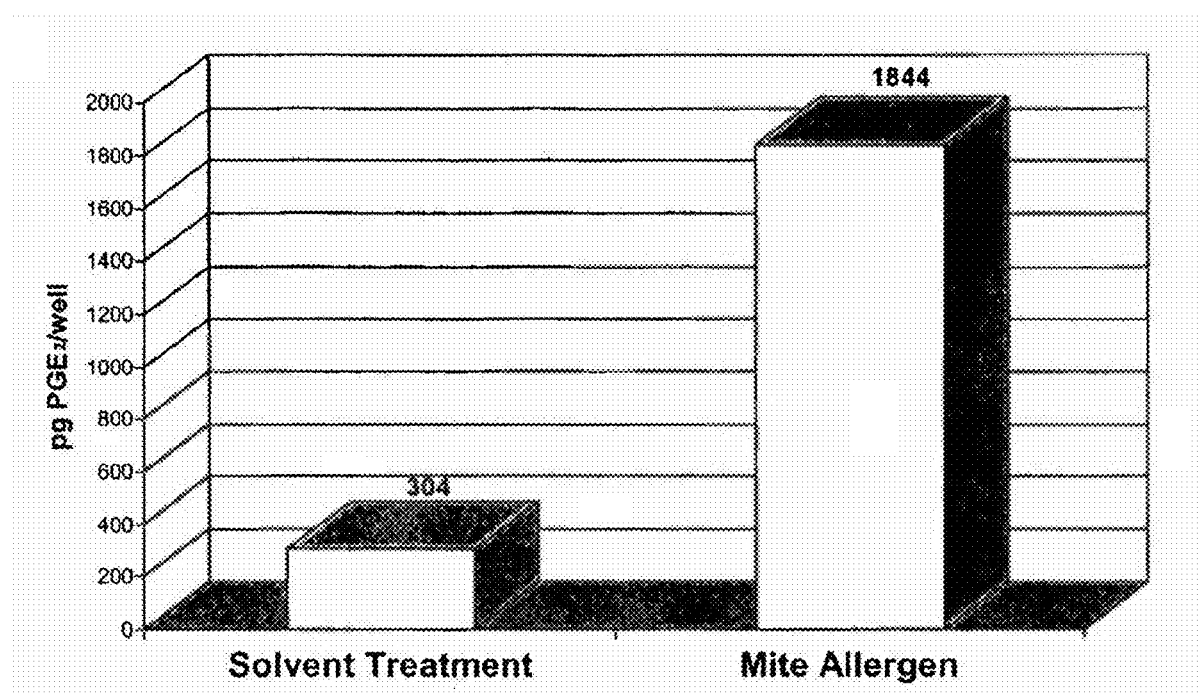
FIG. 5 illustrates the induction of $PGE_2$ synthesis by mite allergen in A549 pulmonary cells treated for 24 hours.

Mite allergen treatment increased PGE$_2$ biosynthesis 6-fold in A549 cells relative to the solvent treated controls (FIG. 5).

Example 14

Hops Derivatives Inhibit Mite Dust Allergen Activation of PGE$_2$ Biosynthesis in A549 Pulmonary Cells Summary—This example illustrates that hops derivatives are capable of inhibiting the PGE$_2$ stimulatory effects of mite dust allergens in A549 pulmonary cells.

Methods

The cell line and testing procedures are as described in Example 14. In addition to mite dust allergen, test materials included Hops fractions (1) alpha hop (1% alpha acids; AA.), (2) aromahop OE (10% beta acids and 2% isomerized alpha kids (3) isohop (isomerized alpha acids; IAA), (4) beta acid solution (beta acids BA), (5) hexahop gold (hexahydro isomerized alpha acids; HHIAA), (6) redihop (reduced isomerized—alpha acids; RIAA), and (7) tetrahop (tetrahydro-iso-alpha acids THIAA). Test materials at a final concentration of 10 μg/mL were added 60 minutes prior to the addition of the mite dust allergen.

Results

Table 7 depicts the extent of inhibition of PGE$_2$ biosynthesis by hops derivatives in A549 pulmonary cells stimulated by mite dust allergen. All hops derivatives were capable of significantly inhibiting the stimulatory effects of mite dust allergens.

TABLE 7

PGE$_2$ inhibition by hops derivatives in A549 pulmonary epithelial cells stimulated by mite dust allergen.

| Test Material | Percent Inhibition of PGE$_2$ BioSynthesis |
| --- | --- |
| Alpha hop (AA) | 81 |
| Aromahop OE | 84 |
| Isohop (IAA) | 78 |
| Beta acids (BA) | 83 |
| Hexahop (HHIAA) | 82 |
| Redihop (RIAA) | 81 |
| Tetrahop (THIAA) | 76 |

In conclusion, it would be useful to identify a natural formulation of compounds that would inhibit expression of COX-2, inhibit prostaglandin synthesis selectively in target cells, or inhibit inflammation response selectively in target cells.

A preferred embodiment comprises compositions containing at least one fraction isolated or derived from hops (*Humulus lupulus*). Examples of fractions isolated or derived from hops are alpha acids, isoalpha acids, reduced isoalpha acids, tetra-hydroisoalpha acids, hexa-hydroisoalpha acids, beta acids, and spent hops. Preferred compounds of fractions isolated or derived from hops, include, but are not limited to, humulone, cohumulone, adhumulone, isohumulone, isocohumulone, isoadhumulone, dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone. Preferred compounds can also bear substituents, such as halogens, ethers, and esters.

It will be readily apparent to those skilled in the art that various changes and modifications of an obvious nature may be made without departing from the spirit of the invention, and all such changes and modifications are considered to fall within the scope of the invention as defined by the appended claims. Such changes and modifications would include, but not be limited to, the incipient ingredients added to affect the capsule, tablet, lotion, food or bar manufacturing process as well as vitamins, herbs, flavorings and carriers. Other such changes or modifications would include the use of other herbs or botanical products containing the combinations of the preferred embodiments disclosed above. Many additional modifications and variations of the embodiments described herein may be made without departing from the scope, as is apparent to those skilled in the art. The specific embodiments described herein are offered by way of example only.

The invention claimed is:

1. A method of treating a pathological condition associated with prostaglandins (PGs) production in a mammal, the method comprising inhibition of inducibility or activity of cyclooxygenase 2 (COX2) by administering to the mammal an effective amount of a composition comprising about 50 to 7500 mg of a compound selected from the group consisting of dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone; wherein the pathological condition is swelling after injury, migraine headache, or other inflammation-associated disorders.

2. The method of claim 1, wherein the compound selected from the group consisting of dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulonc is derived from hops.

3. The method of claim 1, wherein the composition further comprises a pharmaceutically acceptable carrier.

4. The method of claim 1 wherein the composition is administered orally, topically, parenterally, or rectally.

* * * * *